United States Patent
Coughlin

(10) Patent No.: US 11,827,688 B2
(45) Date of Patent: Nov. 28, 2023

(54) DOSING REGIMEN FOR GP100-SPECIFIC TCR—ANTI-CD3 SCFV FUSION PROTEIN

(71) Applicant: IMMUNOCORE LIMITED, Abingdon (GB)

(72) Inventor: Christina Coughlin, Philadelphia, PA (US)

(73) Assignee: Immunocore Limited, Abingdon (GB)

( * ) Notice: Subject to any disclaimer, the term of this patent is extended or adjusted under 35 U.S.C. 154(b) by 749 days.

(21) Appl. No.: 16/305,838

(22) PCT Filed: Jun. 2, 2017

(86) PCT No.: PCT/GB2017/051596
§ 371 (c)(1),
(2) Date: Nov. 29, 2018

(87) PCT Pub. No.: WO2017/208018
PCT Pub. Date: Dec. 7, 2017

(65) Prior Publication Data
US 2020/0040055 A1    Feb. 6, 2020

(30) Foreign Application Priority Data

Jun. 2, 2016  (GB) ..................................... 1609683
Jul. 13, 2016  (GB) ..................................... 1612193
Jul. 14, 2016  (GB) ..................................... 1612260

(51) Int. Cl.
| | | |
|---|---|---|
| *A61P 35/00* | (2006.01) |
| *C07K 14/725* | (2006.01) |
| *A61K 31/4439* | (2006.01) |
| *A61K 38/17* | (2006.01) |
| *A61K 39/395* | (2006.01) |
| *C07K 16/28* | (2006.01) |
| *A61K 39/00* | (2006.01) |

(52) U.S. Cl.
CPC ...... *C07K 14/7051* (2013.01); *A61K 31/4439* (2013.01); *A61K 38/1774* (2013.01); *A61K 39/3955* (2013.01); *A61P 35/00* (2018.01); *C07K 16/2809* (2013.01); *C07K 16/2818* (2013.01); *C07K 16/2827* (2013.01); *A61K 2039/505* (2013.01); *A61K 2039/507* (2013.01); *A61K 2039/545* (2013.01); *C07K 2317/622* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,821,337 A | 10/1998 | Carter et al. |
| 8,105,830 B2 | 1/2012 | Weidanz et al. |
| 8,519,100 B2 | 8/2013 | Jakobsen et al. |
| 9,068,178 B2 | 6/2015 | Jakobsen et al. |
| 10,130,721 B2 | 11/2018 | Jakobsen et al. |
| 10,683,362 B2 | 6/2020 | Pastan et al. |
| 2002/0058253 A1 | 5/2002 | Kranz et al. |
| 2003/0223994 A1 | 12/2003 | Hoogenboom et al. |
| 2004/0253632 A1 | 12/2004 | Rhode et al. |
| 2006/0034850 A1 | 2/2006 | Weidanz et al. |
| 2008/0044413 A1 | 2/2008 | Hammond et al. |
| 2009/0042285 A1 | 2/2009 | Weidanz et al. |
| 2011/0064670 A1 | 3/2011 | Gogineni et al. |
| 2012/0225481 A1 | 9/2012 | Jakobsen et al. |
| 2014/0099699 A1 | 4/2014 | Jakobsen et al. |
| 2014/0154248 A1 | 6/2014 | Pastan et al. |
| 2015/0099775 A1 | 4/2015 | Rice |
| 2019/0247512 A1 | 8/2019 | Jakobsen et al. |
| 2021/0363216 A1 | 11/2021 | Bossi et al. |

FOREIGN PATENT DOCUMENTS

| | | |
|---|---|---|
| EP | 1795599 A1 | 6/2007 |
| WO | WO 1999/060120 A2 | 11/1999 |
| WO | WO 2001/093913 A2 | 12/2001 |
| WO | WO 2002/102299 A2 | 12/2002 |
| WO | WO 03/020763 A2 | 3/2003 |
| WO | WO 2003/070752 A2 | 8/2003 |
| WO | WO 2004/033685 A1 | 4/2004 |
| WO | WO 2004/048410 A2 | 6/2004 |
| WO | WO 2004/074322 A2 | 9/2004 |
| WO | WO 2005/113595 A2 | 12/2005 |
| WO | WO 2005/114215 A2 | 12/2005 |
| WO | WO 2005/120166 A2 | 12/2005 |
| WO | WO 2006/037960 A2 | 4/2006 |
| WO | WO 2006/054096 A2 | 5/2006 |
| WO | WO 2006/129085 A2 | 12/2006 |
| WO | WO 2007/071426 A1 | 6/2007 |
| WO | WO 2007/131092 A2 | 11/2007 |
| WO | WO 2007/143104 A2 | 12/2007 |

(Continued)

OTHER PUBLICATIONS

Sewell., Nature Reviews Immunology 12:669-677, 2012.*
Edwards, J. Mol. Biol. 334:103-118, 2003.*
Kussie et al (Journal of Immunology, 152:146-152, 1994).*
Chen et al, (The EMBO Journal, 14(12):2784-2794, 1995).*
Abstract CT237 Oct. 2014.*
Steiglmaier et al. (Expert Opinion on Biological Therapy, 15:8, 1093-1099 (2015)). (Year: 2015).*

(Continued)

*Primary Examiner* — Zachary S Skelding
(74) *Attorney, Agent, or Firm* — Fenwick & West LLP

(57) ABSTRACT

The present invention relates to the treatment of cancer, particularly gp100 positive cancers. In particular, it relates to a dosage regimen for a T cell redirecting bispecific therapeutic comprising a targeting moiety that binds the YLEPGPVTA (SEQ ID NO:1)-HLA-A2 complex fused to a CD3 binding T cell redirecting moiety.

14 Claims, 5 Drawing Sheets

Specification includes a Sequence Listing.

(56) References Cited

FOREIGN PATENT DOCUMENTS

| WO | WO 2008/089053 A2 | 7/2008 |
|---|---|---|
| WO | WO 2008/135734 A1 | 11/2008 |
| WO | WO 2010/011538 A1 | 1/2010 |
| WO | WO 2010/026377 A1 | 3/2010 |
| WO | WO 2010/133828 A1 | 11/2010 |
| WO | WO 2011/001152 A1 | 1/2011 |
| WO | WO 2011/032013 A1 | 3/2011 |
| WO | WO 2012/154530 A1 | 11/2012 |
| WO | WO 2019/219709 A1 | 11/2019 |

OTHER PUBLICATIONS

Dahan, R. et al., "T-cell-receptor-like antibodies—generation, function and application," Expert Reviews in Molecular Medicine, Feb. 24, 2012, vol. 14:e6, pp. 1-17.

International Search Report and Written Opinion, PCT Application No. PCT/GB2017/051596, dated Sep. 28, 2017, 19 pages.

Liddy, N. et al., "Monoclonal TCR-redirected tumor cell killing", Nature Medicine, May 6, 2012, vol. 18, No. 6, p. 980-987.

Middleton, M. et al., Abstract 1238: "IMCgp100: a novel bispecific biologic for the treatment of malignant melanoma," Proceedings: AACR 104th Annual Meeting 2013, Apr. 2013, vol. 73, Issue 8 Supplement, 2 pages.

Middleton, M. et al., Abstract CT106: "A phase I/IIa study of IMCgp100: Partial and complete durable responses with a novel first-in-class immunotherapy for advanced melanoma," Proceedings: AACR 106th Annual Meeting 2015, Aug. 2015, vol. 75, Issue 15 Supplement, 2 pages.

Salgaller, M. et al., "Immunization against Epitopes in the Human Melanoma Antigen gp100 following Patient Immunization with Synthetic Peptides," Cancer Research, Oct. 15, 1996, vol. 56, Issue 20, pp. 4749-4757.

Sergeeva, A. et al., "An anti-PR1/HLA-A2 T-cell receptor-like antibody mediates complement-dependent cytotoxicity against acute myeloid leukemia progenitor cells," Blood, Apr. 21, 2011, vol. 117, No. 16, pp. 4262-4272.

View of NCT02570308 on Apr. 21, 2016, ClinicalTrials.gov Archive, Apr. 21, 2016 (Apr. 21, 2016), pp. 1-7, XP055402068, Retrieved from the Internet: URL:https://clinicaltrials.gov/archive/NCT02570308/20160421 (retrieved on Aug. 29, 2017).

View of NCT03070392 on May 14, 2017, ClinicalTrials.gov Archive, May 14, 2017 (May 14, 2017), pp. 1-6, XP055402084, Retrieved from the Internet: URL:https://clinicaltrials.gov/archive/NCT03070392/2017 05 14 (retrieved on Aug. 29, 2017).

Wang, M. et al., "Current advances in T-cell-based cancer immunotherapy," Immunotherapy, Dec. 2014, vol. 6, No. 12, pp. 1265-1278.

Adams, Katherine, "Redirected T Cell Activity by High Affinity TCR-Anti-CD3 Bispecific Candidate Therapeutics," Cardiff University for the Degree of Doctor of Philosophy, 2013, pp. 1-290.

Annex 1 (TCR cytokine fusion binding data), cited in Reply of the patent proprietor to the notice of opposition EP 16176246.3, Mar. 16, 2020, 4 pages.

Annex 2 (TCR mimic data), cited in Reply of the patent proprietor to the notice of opposition EP 16176246.3, Mar. 16, 2020, 3 pages.

Apr. 29, 2009 date stamped front page of the Journal of Immunotherapy, vol. 32, No. 4, obtained from the National Library of Medicine, 1 page.

Argos, P., "An investigation of oligopeptides linking domains in protein tertiary structures and possible candidates for general gene fusion," Journal of Molecular Biology, vol. 211, Issue 4, Feb. 20, 1990, pp. 943-958.

Arnett et al., "Crystal structure of a human CD3-ε/δdimer in complex with a UCHT1 single-chain antibody fragment," PNAS, vol. 101, No. 46, Nov. 16, 2004, pp. 16268-16273.

Baeuerle et al., "BiTE: Teaching antibodies to engage T-cells for cancer therapy," Current Opinion in Molecular Therapeutics, 2009, 11(1), 22-30.

Belmont, H., et al., "Potent antitumor activity of a tumor-specific soluble TCR/IL-2 fusion protein," Clinical Immunology, 2006, 121(1):29-39.

Bibollet-Ruche, F., et al., "The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype," Journal of Virology, Oct. 2008, pp. 10271-10278, vol. 82, No. 20.

Bluemel et al., "Epitope distance to the target cell membrane and antigen size determine the potency of T cell-mediated lysis by BiTE antibodies specific for a large melanoma surface antigen," Cancer Immunology, Immunotherapy, vol. 59, pp. 1197-1209 (2010).

Boulter et al., "Stable, soluble T-cell receptor molecules for crystallization and therapeutics," Protein Engineering, Design and Selection, vol. 16, Issue 9, Sep. 1, 2003, pp. 707-711.

Bridgeman et al., "Structural and biophysical determinants of $\alpha\beta$ T-cell antigen recognition," Immunology, vol. 135, Issue 1, Jan. 2012, pp. 9-18.

Card et al., "A soluble single-chain T-cell receptor IL-2 fusion protein retains MHC-restricted peptide specificity and IL-2 bioactivity," Cancer Immunology, Immunotherapy, Apr. 2004, vol. 53, Issue 4, pp. 345-357.

Cassett, F. et al., "A peptide mimetic of an anti-CD4 monoclonal antibody by rational design," Biochemical and Biophysical Research Communications, 307:198-205, 2003.

Chames, P., et al., "Direct selection of a human antibody fragment directed against the tumor T-cell epitope HLA-A1-MAGE-A1 from a nonimmunized phage-Fab library," PNAS, Jul. 5, 2000, pp. 7969-7974, vol. 97, No. 14.

Cheadle, abstract only, "MT-103 Micromet/Medimmune abstract only," Current Opinion in Molecular Therapeutics, Feb. 2006, 8(1):62-68, retrieved online on Nov. 23, 2020 from https://pubmed.ncbi.nlm.nih.gov/16506527/, 1 page abstract only.

Chen et al., "Structural and kinetic basis for heightened immunogenicity of T cell vaccines," Journal of Experimental Medicine, vol. 201, No. 8, Apr. 18, 2005, pp. 1243-1255.

Chlewicki, L.K. et al., "High-affinity, Peptide-specific T Cell Receptors can be Generated by Mutations in CDR1, CDR2 or CDR3," Journal of Molecular Biology, vol. 346, Issue 1, Feb. 11, 2005, pp. 223-239.

Choudhuri et al., "T-cell receptor triggering is critically dependent on the dimensions of its peptide-MHC ligand," Nature, vol. 436, Jul. 28, 2005, pp. 578-582.

Cohen et al., "Generation of Recombinant Immunotoxins for Specific Targeting of Tumor-Related Peptides Presented by MHC Molecules," Methods in Molecular Biology, MIMB, vol. 207, Recombinant Antibodies for Cancer Therapy: Methods and Protocols, pp. 269-282.

Davis et al., "The kinetic-segregation model: TCR triggering and beyond," Nature Immunology, vol. 7., No. 8, 2006, pp. 803-809.

Davis, C. et al., "Immunocytokines: amplification of anti-cancer immunity," Cancer Immunology, Immunotherapy, vol. 52, Issue 5, May 2003, pp. 297-308.

Davis, M. et al., "Ligand Recognition By $\alpha\beta$ T Cell Receptors," Annual Review of Immunology, vol. 16, Apr. 1998, pp. 523-544.

Denkberg et al., "Recombinant antibodies with T-cell receptor-like specificity: Novel tools to study MHC class I presentation," Autoimmunity Reviews, vol. 5, Issue 4, Apr. 2006, pp. 252-257.

Denkberg, G., et al., "Selective Targeting of Melanoma and APCs Using a Recombinant Antibody with TCR-Like Specificity Directed Toward a Melanoma Differentiation Antigen," The Journal of Immunology, 2003, pp. 2197-2207, vol. 171.

Dissertation of Elisa Kieback, "A new safeguard eliminates T cell receptor gene-modified auto-reactive T cells after adoptive therapy," Oct. 23, 2008, 106 pages in total.

Dudley et al., "Adoptive Cell Therapy for Patients with Metastatic Melanoma: Evaluation of Intensive Myeloablative Chemoradiation Preparative Regimens," Journal of Clinical Oncology, Nov. 10, 2008; 26(32), pp. 5233-5239.

Dustin et al., "Receptor Signaling Clusters in the Immune Synapse," Annual Review of Biophysics, 2012, vol. 4, pp. 543-556.

(56) References Cited

OTHER PUBLICATIONS

Epel et al., "A functional recombinant single-chain T cell receptor fragment capable of selectively targeting antigen-presenting cells," *Cancer Immunology, Immunotherapy*, Nov. 2002, 51(10):565-573.

Epel et al., "Targeting TARP, a novel breast and prostate tumor-associated antigen, with T cell receptor-like human recombinant antibodies," *European Journal of Immunology*, vol. 38, Issue 6, Jun. 2008, pp. 1706-1720.

Hoare et al., "Structural basis for a major histocompatibility complex class Ib-restricted T cell response," *Nature Immunology*, vol. 7, No. 3, Mar. 2006, pp. 256-264.

Hong et al., "An MHC interaction site maps to the amino-terminal half of the T cell receptor a chain variable domain," *Cell*, vol. 69, Issue 6, Jun. 12, 1992, pp. 999-1009.

Hülsmeyer et al., "A Major Histocompatibility Complex-Peptide-restricted Antibody and T Cell Receptor Molecules Recognize Their Target by Distinct Binding Modes: Crystal Structure of Human Leukocyte Antigen (HLA)-A1•MAGE-A1 in Complex With FAB-HYB3," *Journal of Biological Chemistry*, vol. 280, No. 4, Jan. 28, 2005, pp. 2972-2980.

Hunder et al., "Treatment of Metastatic Melanoma with Autologous CD4+ T Cells against NY-ESO-1," *The New England Journal of Medicine*, Jun. 19, 2008; 358(25):2698-703.

Huppa et al., "T-cell-antigen recognition and the immunological synapse," *Nature Reviews Immunology*, vol. 3, Dec. 2003, pp. 973-983.

International Search Report and Written Opinion, Patent Cooperation Treaty Application No. PCT/GB2010/000988, dated Oct. 7, 2010, 23 pages.

Kirkwood et al., "Next Generation of Immunotherapy for Melanoma," *Journal of Clinical Oncology*, Jul. 10, 2008, vol. 26, Issue 20, pp. 3445-3455.

Kjer-Nielsen et al., "Crystal structure of the human T cell receptor CD3εγ heterodimer complexed to the therapeutic mAb OKT3," *PNAS*, May 18, 2004, vol. 101, No. 20, pp. 7675-7680.

Klechevsky, E. et al., "Antitumor Activity of Immunotoxins with T-Cell Receptor-like Specificity against Human Melanoma Xenografts," *Cancer Research*, vol. 68, No. 15, Aug. 1, 2008, pp. 6360-6367.

Li, B., et al., "Construction and characterization of a humanized anti-human CD3 monoclonal antibody 12F6 with effective immunoregulation functions," Immunology, 2005, pp. 487-498, vol. 116.

Lipowska-Bhalla, G et al., "Targeted immunotherapy of cancer with CAR T cells: achievements and challenges," *Cancer Immunology, Immunotherapy*, 2012, vol. 61, pp. 953-962.

Löffler et al., "A recombinant bispecific single-chain antibody, CD19 × CD3, induces rapid and high lymphoma-directed cytotoxicity by unstimulated T lymphocytes," *blood*, 2000, 95 (6): 2098-2103.

Lutterbuese et al., "Potent Control of Tumor Growth by CEA/CD3-bispecific Single-chain Antibody Constructs That Are Not Competitively Inhibited by Soluble CEA," *Journal of Immunotherapy*, May 2009, vol. 32, Issue 4, pp. 341-352.

Maccalli, C. et al., "TCR β-Chain Variable Region-Driven Selection and Massive Expansion of HLA-Class 1-Restricted Antitumor CTL Lines From HLA-A 0201+ Melanoma Patients," *The Journal of Immunology*, vol. 158, Issue 12, Jun. 15, 1997, pp. 5902-5913.

MacCallum, R.M. et al., "Antibody-antigen Interactions: Contact Analysis and Binding Site Topography," *Journal of Molecular Biology*, vol. 262, Issue 5, Oct. 11, 1996, pp. 732-745.

Marget, M., et al., "A HLA-Cw6 specific single-chain antibody fragment (scFv) recognizing a natural killer cell receptor epitope," *Molecular Immunology*, 2005, pp. 643-649, vol. 42.

McFarland et al., abstract only, "Ovalbumin(323-339) Peptide Binds to the Major Histocompatibility Complex Class II I-Ad Protein Using Two Functionally Distinct Registers," *Biochemistry* 1999, 38, 50, 16663-16670, 1 page abstract only.

Mølhøj et al., "CD19-/CD3-bispecific antibody of the BiTE class is far superior to tandem diabody with respect to redirected tumor cell lysis," *Molecular Immunology*, vol. 44, Issue 8, Mar. 2007, pp. 1935-1943.

Molloy et al., "Soluble T cell receptors: novel immunotherapies," *Current Opinion in Pharmacology*, vol. 5, Issue 4, Aug. 2005, pp. 438-443.

Morgan, R.A. et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *The Journal of Immunology*, vol. 171, Issue 6, Sep. 15, 2003, pp. 3287-3295.

Mosquera, L., et al., "In Vitro and In Vivo Characterization of a Novel Antibody-Like Single-Chain TCR Human IgG1 Fusion Protein," *The Journal of Immunology*, 2005, pp. 4381-4388.

Neethling, F., et al., "Assessing vaccine potency using TCR mimic antibodies," *Vaccine*, 2008, 26(25):3092-102.

Notice of opposition, European Patent Application No. 16176246.3, dated May 8, 2019, 42 pages.

Notice of opposition, European Patent Application No. EP16176249. 7, dated Jan. 23, 2019, 159 pages.

Offner et al., "Induction of regular cytolytic T cell synapses by bispecific single-chain antibody constructs on MHC class I-negative tumor cells," *Molecular Immunology*, vol. 43, Issue 6, Feb. 2006, pp. 763-771.

O'Herrin et al., "Analysis of the Expression of Peptide-Major Histocompatibility Complexes Using High Affinity Soluble Divalent T Cell Receptors," *Journal of Experimental Medicine*, vol. 186, No. 8, Oct. 20, 1997, pp. 1333-1345.

Ortiz-Sanchez et al., "Antibody—cytokine fusion proteins: applications in cancer therapy," *Expert Opin Biol. Ther.* 2008, 8(5), pp. 609-632.

Padlan et al., "Anatomy of the antibody molecule," *Molecular Immunology*, vol. 31, Issue 3, Feb. 1994, pp. 169-217.

Pan, S-H., et al., "Reduced Background Expression and Improved Plasmid Stability with pET Vectors in BL21 (DE3)," BioTechniques, Dec. 2000, pp. 1234-1238, vol. 29.

Paul, WE., Fundamental Immunology, 3rd Edition, Raven Press, New York, Chapter 9, pp. 292-295, 1993.

Peng et al., "A Single-Chain IL-12 IgG3 Antibody Fusion Protein Retains Antibody Specificity and IL-12 Bioactivity and Demonstrates Antitumor Activity," *The Journal of Immunology*, vol. 1, Issue 1, Jul. 1, 1999, pp. 250-258.

Pule, M. et al., "Artificial T-Cell Receptors," *Cytotherapy*, vol. 5, No. 3, Jan. 2003, pp. 211-226.

Reinherz, E., "αβ TCR-Mediated Recognition: Relevance to Tumor-Antigen Discovery and Cancer Immunotherapy," *Cancer Immunology Research*, Apr. 2015, vol. 3, Issue 4, pp. 305-312.

Richman et al., "Structural features of T cell receptor variable regions that enhance domain stability and enable expression as single-chain VαVβ fragments," *Molecular Immunology*, vol. 46, Issue 5, Feb. 2009, pp. 902-916.

Roosneck et al., "T cell activation by a bispecific anti-CD3/anti-major histocompatibility complex class I antibody," short paper, *European Journal of Immunology*, vol. 20, Iss. 6, Jun. 1990, pp. 1393-1396.

Rudikoff, S. et. al., "Single amino acid substitution altering antigen-binding specificity," Proc. Natl. Acad. Sci. USA, 79(6):1979-1983, Mar. 1982.

Rudolph et al., "The specificity of TCR/pMHC interaction," *Current Opinion in Immunology*, vol. 14, Issue 1, Feb. 1, 2002, pp. 52-65.

Ruf et al., "Characterisation of the new EpCAM-specific antibody HO—3: implications for trifunctional antibody immunotherapy of cancer," *British Journal of Cancer*, 2007, 97(3), 315-321.

Ruf, P. et al., "Induction of a long-lasting antitumor immunity by a trifunctional bispecific antibody," *Blood*, vol. 98, No. 8, Oct. 15, 2001, pp. 2526-2534.

Sadelain, M. et al., "The promise and potential pitfalls of chimeric antigen receptors," *Current Opinion in Immunology*, vol. 21, No. 2, Apr. 2009, pp. 215-223.

Salmeron et al., "A Conformational Epitope Expressed upon Association of CD3-ε with Either CD3-δ or CD3-γY is the Main Target

(56) References Cited

OTHER PUBLICATIONS for Recognition by Anti-CD3 Monoclonal Antibodies," *Journal of Immunology*, vol. 147, No. 9, Nov. 1, 1999, pp. 3047-3052.

Schaft, N. et al., Peptide Fine Specificity of Anti-Glycoprotein 100 CTL is Preserved Following Transfer of Engineered TCRαβ Genes into Primary Human T Lymphocytes, *The Journal of Immunology*, vol. 170, Issue 4, Feb. 15, 2003, pp. 2186-2194.

Schamel et al., "A conformation- and avidity-based proofreading mechanism for the TCR—CD3 complex," *Trends in Immunology*, vol. 27, Issue 4, Apr. 2006, pp. 176-182.

Schlitt, H.J., et al., "Different Activation States of Human Lymphocytes after Antibody-Mediated Stimulation via CD3 and the α/β T-Cell Receptor," *Scandinavian Journal of Immunology*, Dec. 1990, vol. 32, Issue 6, pp. 717-726.

Schodin et al., "Binding properties and solubility of single-chain T cell receptors expressed in *E. coli*," *Molecular Immunology*, vol. 33, Issue 9, Jun. 1996, pp. 819-829.

Seibel et al., "Influence of the NH2-terminal Amino Acid of the T Cell Receptor α Chain on Major Histocompatibility Complex (MHC) Class II + Peptide Recognition," *Journal of Experimental Medicine*, vol. 185, No. 11, Jun. 2, 1997, pp. 1919-1927.

Shalaby et al., "Development of humanized bispecific antibodies reactive with cytotoxic lymphocytes and tumor cells overexpressing the HER2 protooncogene," *Journal of Experimental Medicine*, vol. 175, Issue 1, Jan. 1, 1992, pp. 217-225.

Springer Link, Encyclopedia of Systems Biology, 2013 Edition.

Van Der Merwe et al., "Topology of the CD2—CD48 cell-adhesion molecule complex: implications for antigen recognition by T cells," *Current Biology*, vol. 5, Issue 1, Jan. 1995, pp. 74-84.

Voss C.Y. et al., "Increased Effector-Target Cell Conjugate Formation Due to HLA Restricted Specific Antigen Recognition," *Immunologic Research*, 2009, vol. 45, p. 13-24.

Weber et al., "Class II-restricted T cell receptor engineered in vitro for higher affinity retains peptide specificity and function," *PNAS*, Dec. 27, 2005, vol. 102, No. 52, pp. 19033-19038.

Wen et al., "Targeting activity of a TCR/IL-2 fusion protein against established tumors," *Cancer Immunology, Immunotherapy*, Dec. 2008, vol. 57, Issue 12, pp. 1781-1794.

Willcox et al., "TCR Binding to Peptide-MHC Stabilizes a Flexible Recognition Interface," *Immunity*, vol. 10, Issue 3, Mar. 1999, pp. 357-365.

Willemsen, R., et al., "Selection of Human Antibody Fragments Directed Against Tumor T-Cell Epitopes for Adoptive T-Cell Therapy," 2008, Cytometry Part A, 73A:1093-1099.

Willemsen, R., et al., "T Cell Retargeting with MHC Class I-Restricted Antibodies: The CD28 Costimulatory Domain Enhances Antigen-Specific Cytotoxicity and Cytokine Production," *The Journal of Immunology*, 2005, pp. 7853-7858, vol. 174.

Wolf et al., "BiTEs: bispecific antibody constructs with unique anti-tumor activity," *Drug Discovery Today*, vol. 10, Issue 18, Sep. 15, 2005, pp. 1237-1244.

Woo et al., "GMP production and characterization of the bivalent anti-human T cell immunotoxin, A-dmDT390-bisFv(UCHT1) for phase I/II clinical trials," *Protein Expression and Purification*, vol. 58, Issue 1, Mar. 2008, pp. 1-11.

Wu et al., "Use of bispecific heteroconjugated antibodies (anti-T cell antigen receptor x anti-MHC class II) to study activation of T cells with a full length or truncated antigen receptor zeta-chain," *The Journal of Immunology*, Mar. 15, 1993, vol. 150, No. 6, pp. 2211-2221.

Xiong, C-Y. et al., "Development of tumor targeting anti-MUC-1 multimer: effects of di-scFv unpaired cysteine location of PEGylation and tumor binding," *Protein Engineering, Design & Selection*, vol. 19, No. 8, 2006, pp. 359-367.

Zhu et al., "Direct Measurements of Heterotypic Adhesion between the Cell Surface Proteins CD2 and CD48," *Biochemistry*, 2002, 41, 12163-12170.

Zhu et al., "Engineering high affinity humanized anti-p185$^{HER2}$/anti-CD3 bispecific F(ab')2 for efficient lysis of p185$^{HER2}$ overexpressing tumor cells," *International Journal of Cancer*, vol. 62, Issue 3, Jul. 28, 1995, pp. 319-324.

ClinicalTrials.gov archive, Apr. 2016, NCT02570308, URL:https://clinicaltrials.gov/ct2/history/NCT02570308?A=2&B=2&C=merged#StudyPageTop, 6 pages.

ClinicalTrials.gov archive, Mar. 2016, NCT02535078 and URL:https://clinicaltrials.gov/ct2/history/NCT02535078?A=3&B=3&C=merged#StudyPageTop, 6 pages.

ClinicalTrials.gov archive, Feb. 2016, NCT01211262, URL:https://clinicaltrials.gov/ct2/history/NCT01211262?A=14&B=14&C=merged#StudyPageTop, 6 pages.

Eli Lilly and Company, Lilly and Immunocore Announce Immunotherapy-based Clinical Trial Collaboration in Melanoma, Jun. 29, 2015, URL:https://investor.lilly.com/news/releases/newsreleasedetails/lilly-and-immunocore-based-immunotherapy-based-clinical- [search date : Apr. 27, 2021].

Hinrichs, C.S. et al., "Exploiting the curative potential of adoptive T-cell therapy for cancer," *Immunological Reviews*, vol. 257, Issue 1, Special Issue: Adoptive Immunotherapy for Cancer, Jan. 2014, pp. 56-71.

International Preliminary Report on Patentability, Chapter 1, Patent Cooperation Treaty Application No. PCT/EP2019/062384, dated Nov. 17, 2020, 7 pages.

International Preliminary Report on Patentability, Chapter 1, Patent Cooperation Treaty Application No. PCT/GB2010/000988, dated Nov. 22, 2011, 15 pages.

International Preliminary Report on Patentability, Chapter 1, Patent Cooperation Treaty Application No. PCT/GB2017/051596, dated Dec. 4, 2018, 9 pages.

International Search Report and Written Opinion, Patent Cooperation Treaty Application No. PCT/EP2019/062384, dated Sep. 3, 2019, thirteen pages.

Middleton, M. et al., Abstract CT329: "A phase I/IIa study of IMCgp100: durable responses with a novel first-in-class immunotherapy for advanced melanoma," Proceedings: AACR Annual Meeting 2014, Oct. 2014, vol. 74, Issue 19 Supplement, doi:10.1158/1538-7445.AM2014-CT329.

European Office Action, European Patent Office Application No. EP 17734131.0, dated Apr. 13, 2023, 9 pages.

Riley, T.P., et al., "The intersection of affinity and specificity in the development and optimization of T cell receptor based therapeutics," *Seminars in Cell & Developmental Biology*, vol. 84, Dec. 2018, pp. 30-41.

Algazi, AP, et al., author manuscript of "Clinical outcomes in metastatic uveal melanoma treated with PD-1 and PD-1L antibodies," *Cancer*, vol. 122, Issue 21, Nov. 2016, pp. 3344-3353.

Andreoli, MT, et al., "Epidemiological trends in uveal melanoma," *British Journal of Ophthalmology*, 2015, vol. 99, Issue 11, pp. 1550-1553.

Bohnsack, O., et al., "1070P—Adaptation of the Immune Related Response Criteria: Irrecist," Annals of Oncology, vol. 25, Supplement 4, Sep. 2014, p. iv369, Part of special issue: Abstract Book of the 39th European Society of Medical Oncology Congress (ESMO 2014) Madrid, Spain Sep. 26-30, 2014.

Borghaei, H., et al., "Nivolumab versus Docetaxel in Advanced Nonsquamous Non-Small-Cell Lung Cancer," *The New England Journal of Medicine*, Oct. 2015, 373(17), pp. 1627-1639.

Bossi et al., "Examining the presentation of tumor-associated antigens on peptide-pulsed T2 cells," *OncoImmunology*, 2013, vol. 2, Issue 11, Article: e26840, seven pages.

Boudousquie, C., et al., "Polyfunctional response by ImmTAC (IMCgp100) redirected CD8+ and CD4+ T cells," *Immunology*, vol. 152, Issue 3, Nov. 2017, pp. 425-438.

Bronkhorst, IH, et al, "Detection of M2-Macrophages in Uveal Melanoma and Relation with Survival," *Investigative Ophthalmology & Visual Science*, Feb. 2011, vol. 52, Issue 2, pp. 643-650.

Bronkhorst, IH, et al., "Different Subsets of Tumor-Infiltrating Lymphocytes Correlate with Macrophage Influx and Monosomy 3 in Uveal Melanoma," *Investigative Ophthalmology & Visual Science*, Aug. 2012, vol. 53, Issue 9, pp. 5370-5378.

(56) References Cited

OTHER PUBLICATIONS

Buder, K, et al., "Systemic treatment of metastatic uveal melanoma: review of literature and future perspectives," *Cancer Medicine*, vol. 2, Issue 5, Oct. 2013, pp. 674-686.
Campbell, RJ, et al. & World Health Organization, *Histological Typing of Tumours of the Eye and Its Adnexa*, International Histological Classification of Tumours, Springer-Verlag, Berlin, Heidelberg, 1998, Second Edition.
Carvajal, R., et al., "Effect of Selumetinib vs Chemotherapy on Progression-Free Survival in Uveal Melanoma a Randomized Clinical Trial," *JAMA*. 2014; 311(23):2397-2405.
Carvajal, R., et al., "Metastatic disease from uveal melanoma: treatment options and future prospects," *British Journal of Ophthalmology*, 2017; vol. 101, Issue 1, pp. 38-44.
Carvajal, R., et al., "Safety, efficacy and biology of the gp100 TCR-based bispecific T cell redirector, IMCgp100 in advanced uveal melanoma in two Phase 1 trials," *Journal for ImmunoTherapy of Cancer*, 2017; vol. 5, (Suppl 2):86, P208, pp. 111-112.
Chen, DS, et al., "Oncology Meets Immunology: The Cancer-Immunity Cycle," *Immunity*, vol. 39, Issue 1, Jul. 25, 2013, pp. 1-10.
Damato, BE, et al., "Tebentafusp: T Cell Redirection for the Treatment of Metastatic Uveal Melanoma," *Cancers*, 2019, 11(7), 971, 16 pages.
Deeken, JF, et al., "The Blood-Brain Barrier and Cancer: Transporters, Treatment, and Trojan Horses," *Clinical Cancer Research*, 2007;13 (6):1663-74.
Eisenhauer, EA, et al., "New response evaluation criteria in solid tumours: revised RECIST guideline (version 1.1)," *European Journal of Cancer*, vol. 45, Issue 2, Jan. 2009, pp. 228-247.
Field, MG, et al., author manuscript of "Recent developments in prognostic and predictive testing in uveal melanoma," *Current Opinion in Ophthalmology*, May 2014, vol. 25, Issue 3, pp. 234-239.
Herbst, RS, et al., "Pembrolizumab versus docetaxel for previously treated, PD-L1-positive, advanced non-small-cell lung cancer (KEYNOTE-010): a randomised controlled trial," *Lancet*, vol. 387, Issue 10027, Apr. 9-15, 2016, pp. 1540-1550.
Hoashi, T, et al., "MART-1 is required for the function of the melanosomal matrix protein PMEL17/GP100 and the maturation of melanosomes," *Journal of Biological Chemistry*, vol. 280, Issue 14, Apr. 2005, pp. 14006-14016.
Hodi, FS, et al., "Evaluation of immune-related response criteria and RECIST v1.1 in patients with advanced melanoma treated with pembrolizumab," *Journal of Clinical Oncology*, May 2016, vol. 34, Issue 13, pp. 1510-1517.
Karydis, I., et al., "Clinical activity and safety of pembrolizumab in ipilimumab pre-treated patients with uveal melanoma," *Oncoimmunology*, 2016, vol. 5, Issue 5, e1143997, 9 pages.
Khattak, MA, et al., "Ipilimumab activity in advanced uveal melanoma," *Melanoma Research*, Feb. 2013, vol. 23, Issue 1, pp. 79-81.
Khoja, L., et al., "Meta-analysis in metastatic uveal melanoma to determine progression free and overall survival benchmarks: an international rare cancers initiative (IRCI) ocular melanoma study," *Annals of Oncology*, vol. 30, Issue 8, Aug. 2019, pp. 1370-1380.
Lan, KKG, et al., "Discrete sequential boundaries for clinical trials," *Biometrika*, vol. 70, Issue 3, Dec. 1983, pp. 659-663.
Larkin, J., et al., "Combined nivolumab and ipilimumab or monotherapy in untreated melanoma," *The New England Journal of Medicine*, Jul. 2015, vol. 373, Issue 1, pp. 23-34.
Lee, DW, et al., "Current concepts in the diagnosis and management of cytokine release syndrome," *Blood*, Jul. 2014, vol. 124, No. 2, pp. 188-195.
Luke, JJ, et al., "Clinical activity of ipilimumab for metastatic uveal melanoma: a retrospective review of the Dana-Farber Cancer Institute, Massachusetts General Hospital, Memorial Sloan-Kettering Cancer Center, and University Hospital of Lausanne experience," *Cancer*, vol. 119, Issue 20, Oct. 2013, pp. 3687-3695.
Maat, W., et al., "Monosomy of chromosome 3 and an inflammatory phenotype occur together in uveal melanoma," *Investigative Ophthalmology & Visual Science*, Feb. 2008, vol. 49, Issue 2, pp. 505-510.
Maio, M., et al., "Efficacy and safety of ipilimumab in patients with pre-treated, uveal melanoma," *Annals of Oncology*, vol. 24, Issue 11, Nov. 2013, pp. 2911-2915.
Middleton, M., et al., "Tebentafusp, a TCR/anti-CD3 bispecific fusion protein targeting gp100, potently activated anti-tumor immune responses in patients with metastatic melanoma," *Clinical Cancer Research*, Nov. 2020, vol. 26, Issue 22, pp. 5869-5878.
Motzer, RJ, et al., "Nivolumab versus Everolimus in Advanced Renal-Cell Carcinoma," *The New England Journal of Medicine*, Nov. 2015, vol. 373, No. 19, pp. 1803-1813.
Nishino, A., et al., "Developing a common language for tumor response to immunotherapy: immune-related response criteria using unidimensional measurements," *Clinical Cancer Research*, vol. 19, Issue 14, Jul. 2013, pp. 3936-3943.
Patel, M., et al., "Therapeutic implications of the emerging molecular biology of uveal melanoma," *Clinical Cancer Research*, vol. 17, Issue 8, Apr. 2011, pp. 2087-2100.
Rastrelli, M., et al., "Melanoma: epidemiology, risk factors, pathogenesis, diagnosis and classification," *In Vivo*, vol. 28, Issue 6, Nov. 2014, pp. 1005-1011.
Robert, C., et al., "Nivolumab in previously untreated melanoma without BRAF mutation," *The New England Journal of Medicine*, Jan. 2015, vol. 372, No. 4, pp. 320-330.
Sato et al., "Redirected T cell lysis in patients with metastatic uveal melanoma with gp100-directed TCR IMCgp100: Overall survival findings," *Journal of Clinical Oncology*, vol. 36, No. 15, Supplement, May 20, 2018, p. 9521.
Schneider, SW, et al., "Glioblastoma cells release factors that disrupt blood-brain barrier features," *Acta Neuropathologica*, Jan. 2004;107(3):272-76.
Simka, M., "Blood brain barrier compromise with endothelial inflammation may lead to autoimmune loss of myelin during multiple sclerosis," *Current Neurovascular Research*, vol. 6, No. 2, 2009, pp. 132-139.
Stebbings, R., et al., "'Cytokine storm' in the Phase 1 trial of monoclonal antibody TGN1412: better understanding the causes to improve preclinical testing of immunotherapeutics," *The Journal of Immunology*, vol. 179, Issue 5, Sep. 2007, pp. 3325-3331.
Takase, H., et al., "Thymic expression of peripheral tissue antigens in humans: a remarkable variability among individuals," *International Immunology*, vol. 17, Issue 8, Aug. 2005, pp. 1131-1140.
Therasse, P., et al., "New Guidelines to Evaluate the Response to Treatment in Solid Tumors," *JNCI: Journal of the National Cancer Institute*, vol. 92, Issue 3, Feb. 2, 2000, pp. 205-216.
Tumeh, PC, et al., "PD-1 blockade induces responses by inhibiting adaptive immune resistance," *Nature*, 2014; vol. 515, Issue 7528, pp. 568-571.
Valpione, S., et al., "Development and external validation of a prognostic nomogram for metastatic uveal melanoma," *PLOS One*, Mar. 2015, vol. 10, Issue 3, e0120181, 12 pages.
Van Dinten, LC, et al., "Uveal and cutaneous melanoma: shared expression characteristics of melanoma-associated antigens," *Investigative Ophthalmology & Visual Science*, Jan. 2005, vol. 46, pp. 24-30.
Wagner, SN, et al., "Analysis of Pmel17/gp100 expression in primary human tissue specimens: implications for melanoma immuno- and gene-therapy," *Cancer Immunology, Immunotherapy*, vol. 44, Jun. 1997, pp. 239-247.
Wolchok, JD, et al., "Guidelines for the evaluation of immune therapy activity in solid tumors: immune-related response criteria," Clinical Cancer Research, vol. 15, Issue 23, Dec. 2009, pp. 7412-7420.
Wolchok, JD, et al., "Nivolumab plus ipilimumab in advanced melanoma," *The New England Journal of Medicine*, Jul. 2013, vol. 369, No. 2, pp. 122-133.
Woodman, SE, author manuscript of "Metastatic uveal melanoma: biology and emerging treatments," *The Cancer Journal*, Mar./Apr. 2012, vol. 18, Issue 2, pp. 148-152.
Yu, FX, et al., "Mutant Gq/11 promote uveal melanoma tumorigenesis by activating YAP," *Cancer Cell*, vol. 25, Issue 6, Jun. 2014, pp. 822-830.

(56) References Cited

OTHER PUBLICATIONS

Zimmer, L., et al., "Phase II DeCOG study of ipilimumab in pretreated and treatment-naïve patients with metastatic uveal melanoma," *PLOS One*, Mar. 2015, vol. 10, Issue 3, e0118564, 13 pages.

Augsberger, JJ, et al., "Effectiveness of Treatments for Metastatic Uveal Melanoma," *American Journal of Ophthalmology*, vol. 148, Issue 1, Jul. 2009, pp. 119-127.

Bargou, R., et al., "Tumor Regression in Cancer Patients by Very Low Doses of a T Cell-Engaging Antibody," *Science*, Aug. 2008, vol. 321, Issue 5891, pp. 974-977.

Dunavoelgyi, R., et al., "Local Tumor Control, Visual Acuity, and Survival After Hypofractionated Stereotactic Photon Radiotherapy of Choroidal Melanoma in 212 Patients Treated Between 1997 and 2007," *International Journal of Radiation Oncology, Biology and Physics*, vol. 81, Issue 1, Sep. 2011, pp. 199-205.

ECOG-ACRIN Cancer Research Group, "ECOG Performance Status Scale," date unknown, 3 pages, [Online] [Retrieved on Jun. 21, 2023] Retrieved from the Internet <URL: http://ecog-acrin.org/resources/ecogperformance-status>.

Edge, SB, et al. (Eds.), "Malignant Melanoma of the Uvea," *AJCC Cancer Staging Manual*, 7th edition, New York, NY: Springer. 2010:547-59.

Furney SJ, et al., "The mutational burden of acral melanoma revealed by whole-genome sequencing and comparative analysis," *Pigment Cell & Melanoma Research*, vol. 27, Issue 5, Sep. 2014, pp. 835-838.

Jarosinski, KW, et al., "Interferon regulatory factor-1 is required for interferon-gamma-induced MHC class I genes in astrocytes," *Journal of Neuroimmunology*, vol. 122, Issues 1-2, Jan. 2002, pp. 74-84.

Kawakami, Y., et al., "Immunobiology of Human Melanoma Antigens MART-1 and gp100 and their Use for Immuno-Gene Therapy," *International Reviews of Immunology*, 1997, vol. 14, Issue 2-3, pp. 173-192.

Lampson, LA, et al., "Monoclonal antibody analysis of MHC expression in human brain biopsies: tissue ranging from "histologically normal" to that showing different levels of glial tumor involvement," *The Journal of Immunology*, vol. 136, Issue 11, Jun. 1986, pp. 4054-4062.

Lens, M., "The role of vaccine therapy in the treatment of melanoma," *Expert Opinion on Biological Therapy*, 2008, vol. 8, Issue 3, pp. 315-323.

McAlpine, C., et al., "Biomarker Strategy to Guide Clinical Development of ImmTAC™ molecules, A Novel Class of Bispecific T Cell Engaging Biologic Drugs," American Academy for Cancer Research Annual Meeting, Washington, DC. Apr. 2017, 1 page.

Middleton, D., et al., "New allele frequency database: http://www.allelefrequencies.net," *Tissue Antigens*, vol. 61, Issue 5, May 2003, pp. 403-407.

Middleton, M.R., et al., "Poster presentation: Safety and efficacy of IMCgp100, a soluble HLA-A2 restricted gp100-specific T cell receptor-CD3 therapeutic, in patients with advanced uveal melanoma," Society for Melanoma Research Annual Meeting, San Francisco, CA, Nov. 2015b, 1 page.

Middleton, M.R., et al., "A phase I/IIa study of IMCgp100: partial and complete durable responses with a novel first-in-class immunotherapy for advanced melanoma," American Academy for Cancer Research Annual Meeting, Philadelphia, PA, Apr. 2015, pp. 1-37.

Middleton, M.R., et al., "Abstract 3016: Safety, Pharmacokinetics and Efficacy of IMCgp100, a First-in-Class Soluble TCR Anti-CD3 Bispecific T Cell Redirector with Solid Tumour Activity: Results from the FIH Study in Melanoma," American Society for Clinical Oncology, 2016 Annual Meeting, Chicago, USA, 1 page.

Middleton, M.R., et al., "Abstract 9523: Relationship between clinical efficacy and AEs of IMCgp100, a novel bispecific TCR-anti-CD3, in patients with advanced melanoma," American Society for Clinical Oncology Annual Meeting, Chicago, IL, Jun. 2019b, 1 page.

Middleton, M.R., et al., "Abstract 9530: Pharmacodynamic effect of IMCgp100 (TCR-CD3 bispecific) on peripheral cytokines and association with overall survival in patients with advanced melanoma," American Society for Clinical Oncology Annual Meeting, Chicago, IL. Jun. 2019a, 1 page.

Ministry of Health and Welfare of Japan, "The General Guidelines for Clinical Evaluation of New Drugs," Issue Number Yaku Shin-Yaku No. 43, Notification from Director of New Drugs Division, Pharmaceutical Affairs Bureau, Ministry of Health and Welfare of Japan, to Directors of Prefectural Departments responsible for health, 1992, pp. 1-12, 26 page with machine translation.

Murphy, K., et al., "Alloreactive T cells recognizing nonself MHC molecules are very abundant," *Janeway's Immunobiology*, 8th ed. New York, NY: Garland Science; 2011:239-40.

Nagorsen, D., et al., "Immunotherapy of lymphoma and leukemia with T-cell engaging BiTE antibody blinatumomab," *Leukemia & Lymphoma*, 2009, vol. 50, Issue 6, pp. 886-891.

Nicholas, M., et al., "Abstract 9570: Prognosticators of first line treatment for metastatic uveal melanoma (MUM)," American Society of Clinical Oncology, Annual meeting 2016, vol. 34, Issue 15 suppl., 3 pages.

O'Brien, PC, et al., "A multiple testing procedure for clinical trials," *Biometrics*, 1979;35(3):549-56.

Ramaiya, KJ, et al., "Current management of uveal melanoma," *Expert Review of Ophthalmology*, Dec. 2007, vol. 2, Issue 6, pp. 939-946.

Sato, T., et al., "Abstract 9531: Intra-Patient Escalation Dosing Strategy with IMCgp100 Results in Mitigation of T cell Based Toxicity and Preliminary Efficacy in Advanced Uveal Melanoma," American Society for Clinical Oncology Annual Meeting, Chicago, IL. Jun. 2017, 1 page.

Shoushtari, A.N., et al. "A Phase 1 study of IMCgp100, a soluble HLA-A2 restricted gp100-specific T cell receptor-CD3 therapeutic with solid tumor activity in patients with advanced uveal melanoma," Society for Melanoma Research International Congress, Annual Meeting 2016 (Oral presentation), pp. 1-20.

Shoushtari, AN, et al., "GNAQ and GNA11 mutations in uveal melanoma," *Melanoma Research*, Dec. 2014, vol. 24, Issue 6, pp. 525-534.

Singh, AD, et al., "Incidence of uveal melanoma in the United States: 1973-1997," *Ophthalmology*, vol. 110, Issue 5, May 2003, pp. 956-961.

Singh, AD, et al., "Uveal Melanoma: Trends in Incidence, Treatment, and Survival," *Ophthalmology*, vol. 118, Issue 9, Sep. 2011, pp. 1881-1885.

* cited by examiner

Figure 1

Amino acid sequence of the alpha chain extracellular domain of the reference gp100 TCR (SEQ ID No; 2);

SQQGEEDPQALSIQEGENATMNCSYKTSINNLQWYRQNSGRGLVHLILIRSNEREKHSGR
LRVTLDTSKKSSSLLITASRAADTASYFCATDGDTPLVFGKGTRLSVIANIQKPDPAVYQ
LRDSKSSDKSVCLFTDFDSQTNVSQSKDSDVYITDKCVLDMRSMDFKSNSAVAWSNKSDF
ACANAFNNSIIPEDTFFPSPESS

Figure 2

Amino acid sequence of the beta chain extracellular domain of the reference gp100 TCR (SEQ ID No; 3);

DGGITQSPKYLFRKEGQNVTLSCEQNLNHDAMYWYRQDPGQGLRLIYYSQIVNDFQKGDI
AEGYSVSREKKESFPLTVTSAQKNPTAFYLCASSIGGPYEQYFGPGTRLTVTEDLKNVFP
PEVAVFEPSEAEISHTQKATLVCLATGFYPDHVELSWWVNGKEVHSGVCTDPQPLKEQPA
LNDSRYALSSRLRVSATFWQDPRNHFRCQVQFYGLSENDEWTQDRAKPVTQIVSAEAWGR
AD

*Figure 3*

Amino acid sequence of a gp100-specific TCR α chain (SEQ ID No: 4):

AQQGEEDPQALSIQEGENATMNCSYKTSINNLQWYRQNSGRGLVHLILIRSNEREKHSGRLRVTLD
TSKKSSSLLITASRAADTASYFCATDGSTPMQFGKGTRLSVIANIQKPDPAVYQLRDSKSSDKSVC
LFTDFDSQTNVSQSKDSDVYITDKCVLDMRSMDFKSNSAVAWSNKSDFACANAFNNSIIPEDT

*Figure 4*

Amino acid sequence of an anti-CD3 scFv antibody fragment (bold type) fused via a linker namely GGGGS (underlined) at the N-terminus of a gp100-specific TCR β chain (SEQ ID No 5):

**AIQMTQSPSSLSASVGDRVTITCRASQDIRNYLNWYQQKPGKAPKLLIYYTSRLESGVPS
RFSGSGSGTDYTLTISSLQPEDFATYYCQQGNTLPWTFGQGTKVEIKGGGGSGGGGSGGG
GSGGGGSGGGSEVQLVESGGGLVQPGGSLRLSCAASGYSFTGYTMNWVRQAPGKGLEWVA
LINPYKGVSTYNQKFKDRFTISVDKSKNTAYLQMNSLRAEDTAVYYCARSGYYGDSDWYF
DVWGQGTLVTVSS**GGGGSDGGITQSPKYLFRKEGQNVTLSCEQNLNHDAMYWYRQDPGQG
LRLIYYSWAQGDFQKGDIAEGYSVSREKKESFPLTVTSAQKNPTAFYLCASSWGAPYEQY
FGPGTRLTVTEDLKNVFPPEVAVFEPSEAEISHTQKATLVCLATGFYPDHVELSWWVNGK
EVHSGVCTDPQPLKEQPALNDSRYALSSRLRVSATFWQDPRNHFRCQVQFYGLSENDEWT
QDRAKPVTQIVSAEAWGRAD

*Figure 5*

Observation of toxicities which include severe and/or serious hypotension are confined to the first weeks of dosing

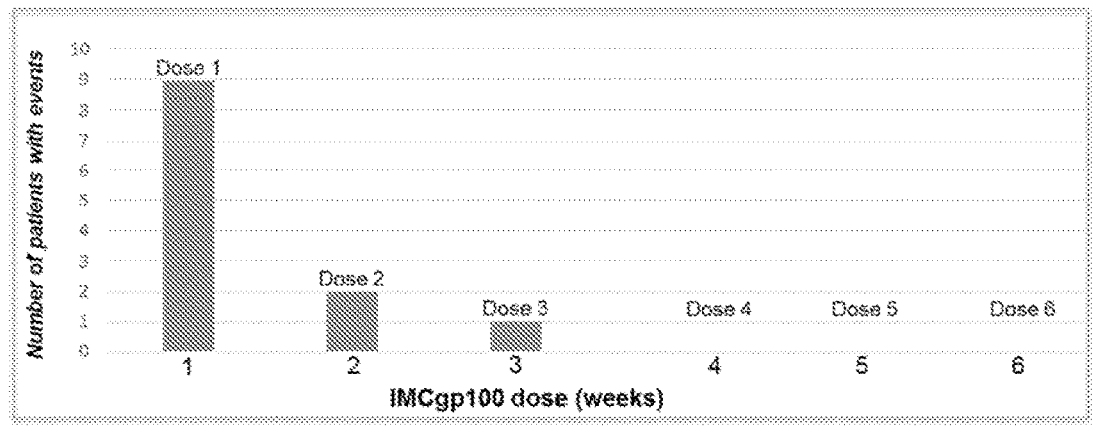

*Figure 6*

Lymphocyte trafficking from the periphery following a first dose of IMCgp100. Mean peripheral lymphocyte counts in blood at baseline (day 1 pre-dose) and at various time-points following the first dose of IMCgp100 (4h, 8h and/or 10h, 24h, 48h and day 8 post-dose) in a patient group with reported severe and/or serious hypotension (grey squares, n=6) compared to a patient group with no reported hypotension (black circles, n=5). Point of dosing indicated. Day 8 sample is pre-second dose.

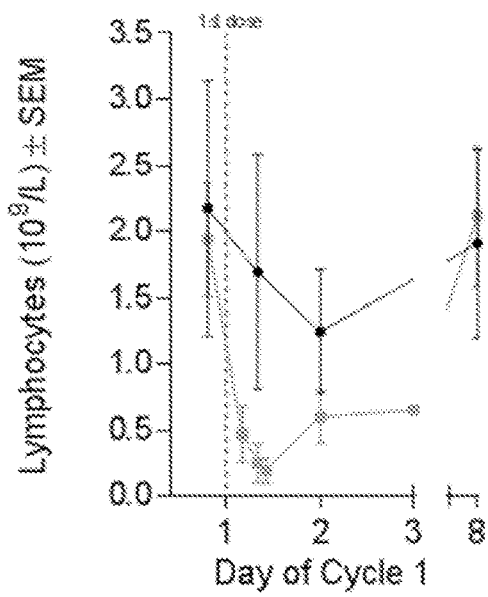

T cell proliferation with IMCgp100 in the presence or absence of anti-CTLA-4, and at two different epitope concentrations Improved T cell killing of melanoma lines (PD-L1/PD-1 pathway)

Cytokine secretion with IMCgp100 + anti-CTLA-4

☐ no IMCgp100 + $10^{-7}$M pep
■ 80pM IMCgp100 + $10^{-7}$M pep
▨ 80pM IMCgp100 + $10^{-8}$M pep Cytokine secretion with IMCgp100 + anti-PD-L1

☐ no IMCgp100
■ IMCgp100 + anti-PD-L1

DOSING REGIMEN FOR GP100-SPECIFIC TCR—ANTI-CD3 SCFV FUSION PROTEIN

CROSS-REFERENCE TO RELATED APPLICATIONS

This application is the National Stage of International Application No. PCT/GB2017/051596, filed Jun. 2, 2017, which claims the benefit of and priority to Great Britain Patent Application Serial Nos. 1609683.6, filed on Jun. 2, 2016, 1612193.1, filed Jul. 13, 2016, and 1612260.8, filed on Jul. 14, 2016, the contents of which are incorporated by reference in their entirety.

SEQUENCE LISTING

The instant application contains a Sequence Listing which has been filed electronically in ASCII format and is hereby incorporated by reference in its entirety. Said ASCII copy, created on Nov. 29, 2018, is named 42183US_Sequence_Listing.txt and is 11,740 bytes in size.

The present invention relates to the treatment of cancer, particularly gp100 positive cancers. In particular, it relates to a dosage regimen for a T cell redirecting bispecific therapeutic comprising a targeting moiety that binds the YLEPGPVTA (SEQ ID NO:1)-HLA-A2 complex fused to a CD3 binding T cell redirecting moiety.

The human glycoprotein 100 (gp100) is one of a panel of melanoma-associated antigens to which the body can mount a natural immune response. The protein is a 661 amino acid melanosomal membrane-associated glycoprotein which is expressed in normal melanocytes and widely overexpressed on the majority of melanoma cancer cells. For example, one study (Trefzer et al., (2006) Melanoma Res. 16(2): 137-45) found that 82% of 192 melanoma metastases from 28 melanoma patients expressed gp100. Several studies reported higher expression levels of gp100 in melanoma tissues (Hofbauer et al., (2004) J Immunother. 27(1): 73-78, Barrow et al., (2006) Clin Cancer Res. 12:764-71). Whilst the majority of gp100 positive cancers are melanomas, the literature also contains numerous reports of other forms of cancer such as clear cell sarcoma and various brain cancer subtypes that express gp100 as detected for instance by immunohistochemistry with an antibody called HMB-45, a widely used gp100 specific diagnostic antibody (Huang et al., (2015) Int J Clin Exp Pathol. 8(2):2171-5, Ozuguz et al., (2014) Indian Dermatol Online J 5(4): 488-90, Taddei et al., Appl Immunohistochem Mol Morphol (2001) 9(1):35-41). The exact function of the protein is unknown but it appears to be involved in melanosome maturation (Hoashi et al., 2005; Kawakami and Rosenberg, 1997). The gp100 antigen has been, and continues to be, the target of a number of immunotherapy-based melanoma clinical trials.

Early gp100 targeted immunotherapy involved vaccination strategies with peptides or viruses expressing the gp100 protein in its entirety, or portions thereof (reviewed in (Lens (2008) Expert Opin Biol Ther. 8(3): 315-323.)). These trials have had limited success which is thought to be a result of the generation of an insufficient immune response rather than a reflection on the validity of the target. Therefore, the principle of using gp100 as a melanoma target remains a valid approach for melanoma specific immunotherapy.

The development of a novel bispecific therapeutic comprising a T cell receptor-based, gp100 specific, targeting moiety fused to a CD3 binding T cell redirecting moiety provides a new treatment option (Liddy et al., (2012). Nat Med. 8: 980-987). The mechanism of action of such a therapeutic is significantly different to other immunotherapy predecessors and results in the rapid and potent redirection of non-gp100 specific T cells to kill gp100 positive cells in vitro; thus there is a sound rationale for expecting both improved clinical efficacy results in patients and on-target, off-tumour toxicities from activity against gp100 positive normal tissues such as skin melanocytes.

The peptide YLEPGPVTA (SEQ ID No: 1) corresponds to amino acid residue numbers 280-288 of gp100. The YLEPGPVTA (SEQ ID No: 1) peptide is presented by Class I HLA molecules on gp100+/HLA-A*02+ cancer cells (Salgaller et al., (1996) Cancer Res 56: 4749-4757). WO2011/001152 describes TCRs which bind the YLEPGPVTA (SEQ ID NO:1) peptide presented as a peptide-HLA-A*02 complex. The TCRs are mutated relative to a native gp100 TCR alpha and/or beta variable domains to have improved binding affinities for, and/or binding half-lives for the complex, and can be associated (covalently or otherwise) with a therapeutic agent. One such therapeutic agent is an anti-CD3 antibody, or a functional fragment or variant of said anti-CD3 antibody such as a single chain variable fragment (scFv). The anti-CD3 antibody or fragment may be covalently linked to the C- or N-terminus of the alpha or beta chain of the TCR. Such TCRs have been used to treat melanoma in patients (clinical trial identifier NCT01211262).

IMCgp100 is a T cell redirecting bispecific therapeutic agent comprising a soluble affinity enhanced TCR that binds to the YLEPGPVTA (SEQ ID NO:1) peptide-HLA-A*02 complex, fused to an anti-CD3 scFv. IMCgp100 has been shown to function in vitro by binding to gp100 positive target cells and inducing killing via the recruitment of both tumour-specific and non-tumour-specific T cells. Once bound to the peptide-HLA-A*02 complex on the surface of a gp100 positive target cell, IMCgp100 crosslinks the targeted cell to the T cell through the interaction of the anti-CD3 scFv portion of the molecule. Crosslinking of the two cells via the bi-specific therapeutic results in the formation of an immune synapse, activation of the T cell and redirection of a T cell response against the gp100 positive target cell. IMCgp100 can activate both CD4$^+$ and CD8$^+$ T cells; however, its primary function is to induce CD8$^+$ T cell responses. CD8$^+$ T cells, also known as cytotoxic T lymphocytes (CTL), play an essential role in the natural immune system's repertoire for fighting cancer. CTLs are cytolytic and function to induce lysis of the tumour cell through the apoptotic pathway.

As mentioned above, gp100 is expressed in normal healthy cells including melanocytes, which raises the possibility of on-target, off-tumour reactivity in a clinical setting. Expression levels of gp100 in melanocytes are known to be lower than in tumours. During preclinical testing of IMCgp100, it was confirmed that IMCgp100 was able to redirect T cell activity against normal melanocytes, but at a lower potency than tumour cells, potency in this context being directly proportional to the number of epitopes displayed on the surface of the target cells (Liddy et al., (2012). Nat Med. 8: 980-987). While these data indicate a potential therapeutic window between on-tumour and off-tumour reactivity, on-target, off-tumour reactivity cannot be excluded with IMCgp100 treatment. Any reactivity to melanocytes in the skin during clinical testing would be expected to manifest as skin-related toxicity such as rash, vitiligo and the effects of localised cytokine and chemokine release, which may be managed with hydrocortisone treatment. No other safety concerns were identified during in vitro preclinical testing of IMCgp100, including no evidence for off-target cross reactivity. IMCgp100 was approved for clinical testing based on this data. As will be appreciated by those skilled in the art, suitable therapeutic dose levels cannot be predicted a priori and depend on both the mechanism of action of the drug and the expression profile of the target antigen. It therefore follows that, whilst the on-target, off-tumour toxicities of numerous gp100 specific vaccines and autologous T cell therapies that have been evaluated in the clinic are known, it would still be impossible to predict an appropriate therapeutic dose for a T cell redirecting therapeutic a priori. This is because, whilst vaccines and autologous T cell therapies result in only a small proportion of T cells in the patient being able to recognise the gp100 positive cells, a T cell redirecting therapeutic can in theory provide every CD3 positive T cell in the patient the capacity to recognise and react to gp100 positive cells.

The safety and tolerability of IMCgp100 in patients with advanced melanoma has been investigated in a Phase I trial (clinical trial identifier NCT01211262). Interim results of this study have been presented (Middleton et al., (2015) Cancer Res 2015; 75 (15 Suppl):Abstract nr CT106). The maximum tolerated dose for weekly administration was determined to be 600 ng/kg, which was transitioned to a recommended phase II dose (RP2D) of 50 µg per dose, irrespective of the patient's weight. During the dose escalation portion of the study, severe (grade ¾) hypotension was observed as the main dose limiting toxicity. A cohort of patients subsequently received weekly dosing at RP2D and further episodes of severe hypotension were reported. Other common adverse events included rash, pruritus, pyrexia and oedema. Adverse events typically manifested shortly after the first or second dose of drug. Additional weekly doses of IMCgp100 beyond dose 2 resulted in fewer adverse reactions and a general amelioration in the severity of these events. To increase tolerability during early doses the first weekly dose of IMCgp100 was reduced by 20% to 40 µg as is common practice, followed by dosing at RP2D in subsequent weeks. However, cases of severe hypotension continued to occur. Expression of gp100 in melanocytes within the skin provides a large sink of antigen positive cells in the largest organ in the body. Potent targeting of gp100 positive cells by IMCgp100 leads to redirected T cell activity against gp100 positive skin melanocytes. This manifests as skin-related toxicity in patients. Analysis of patient serum and biopsy samples demonstrate localised cytokine and chemokine release within both skin and tumours resulting in a high volume of T cells being trafficked from the peripheral circulation into tissues within an extremely short space of time; the substantial fluid shifts associate with this rapid T cell migration result in hypotension.

In a first aspect, the present invention provides a T cell redirecting bispecific therapeutic which comprises (i) a targeting moiety that binds the YLEPGPVTA (SEQ ID NO:1)-HLA-A2 complex fused to (ii) a CD3 binding T cell redirection moiety, for use in a method of treating gp100 positive cancer in a patient comprising administering the bispecific therapeutic to said patient, wherein each dose is administered every 5-10 days, at least the first and second doses are below 40 µg and the second dose is higher than the first dose.

The inventors have surprisingly found an intra-patient dose escalation regimen that provides improved tolerability for treating gp100 positive tumours with a bi-specific therapeutic employing a T cell redirection mediated mechanism-of-action. The present invention provides an escalating dosage regimen in which undesirable side effects, such as severe hypotension, are significantly reduced. The dosage regimen is useful to reduce the severity of on-target, off-tumour toxicity in patients thereby reducing the need for patients to remain hospitalised and/or be admitted to intensive care during the first few weeks of treatment. An additional and surprising benefit is that, through ameliorating the effects on on-target, off-tumour T cell activity by use of the dosing regimen, patients can subsequently safely tolerate higher overall therapeutic dose levels than the existing R2P2 of 50 µg, which is expected to result in improved clinical efficacy. Without wishing to be bound by theory, the inventors hypothesise that the dose limiting toxicity of hypotension is driven by the $C_{max}$ exposure levels of the bi-specific therapeutic, the presence of a large amount of gp100 positive melanocytes within the skin compartment and the extent of tumour gp100 expression within the patient with respect to both the patient's disease burden and the expression level of gp100 within the patients tumours. The inventors believe that the dosing regimen may allow sufficient destruction of normal skin melanocytes expressing high levels of gp100 to subsequently allow safer administration of higher therapeutic doses which result in improved targeting of remaining gp100 positive tumour cells and thereby improve clinical efficacy.

The inventors observed that patients with tumours with larger diameters or higher overall disease burden experienced objective tumour responses at higher overall exposures to IMCgp100 than patients with smaller tumours or disease burden. Based on this data, the inventors hypothesise that an increased exposure to drug in the weeks following mitigation of the previously dose limiting toxicities through use of the dosing regimen of the invention may lead to an enhanced tumour response.

In the present invention, the bispecific therapeutic may be administered as follows:
(a) at least one first dose in the range of from 10-30 µg;
(b) at least one second dose in the range of from 20-40 µg, wherein the or each second dose is higher than the first dose; and then
(c) at least one dose of at least 50 µg.

In the present invention, the respective doses may be expressed as a specified weight of therapeutic irrespective of the patient's weight or whether the same amount of therapeutic would be administered if calculated through one of the other methods routinely used to calculate an appropriate dosage for a patient such as weight of therapeutic per Kg of body weight, body surface area or lean muscle mass etc. It is preferred if the specified weight of therapeutic is administered at weekly intervals, e.g. on days 1, 8, 15, 22, etc of the treatment regimen but the dosing interval could be longer or shorter. The dosing interval may depend on the antigen binding characteristics of the T cell redirecting bispecific therapeutic and its clearance half-life. Thus, each dose may be administered every 6-9 or 6-8 days. Preferably each dose is administered every 7 days. The respective doses may be separated by different intervals. Alternatively, they may be separated by the same interval.

The first dose may be in the range of from 10-30 µg. It may be in the range of from 13-27 µg, 15-25 µg or 18-22 µg. The dose may be 15, 16, 17, 18, 19, 20, 21, 22, 23, 24 or 25 µg. One preferred first dose is 20 µg, which may be administered on a weekly basis. One first dose may be administered. Alternatively, more than one first dose, preferably 2-5 first doses and more preferably two first doses, may be administered. It is preferred that, if two or more first doses are administered, they are the same. However, they may be different.

The second dose may be in the range of from 20-40 μg and may be higher than the first dose. The second dose may be 1, 2, 3, 4, 5, 6, 7, 8, 9 or 10 μg higher than the first dose. It may be in the range of from 23-37 μg, 25-35 μg or 28-32 μg. The subsequent dose may be 25, 26, 27, 28, 29, 30, 31, 32, 33, 34 or 35 μg. One preferred second dose is 30 μg, which may be administered on a weekly basis. One second dose may be administered. Alternatively, more than one second dose, preferably 2-5 second doses and more preferably two second doses, may be administered. It is preferred that, if two or more second doses are administered, they are the same. However, they may be different.

The dose after the second dose may be at least 50 μg. It may be in the range of from 50-300 μg, 50-250 μg, 50-200 μg, 50-150 μg, 50-100 μg, 50-90 μg, 50-80 μg, 50-70 μg or 50-60 μg. The dose may be at least 50, 55, 60, 65, 70, 75, 80, 85, 90, 95, 100, 110, 120, 130, 140, 150, 160, 170, 180, 190, 200, 210, 220, 230, 240 or 250 μg. One preferred dose after the second dose is 50 μg. Another is 60 μg and a yet further is 70 μg. The same dose may be used subsequently. Alternatively, the dose may be escalated. For example, the dose may be 5, 10, 15, 20, 30, 40 or 50 μg higher.

The first dose may be 20 μg, the second dose may be 30 μg and/or the dose after the second dose may be 50 μg or greater.

The T cell redirecting bispecific therapeutic useful in the present invention comprises (i) a targeting moiety that binds the YLEPGPVTA (SEQ ID NO:1)-HLA-A2 complex fused to (ii) a CD3 binding T cell redirection moiety.

The targeting moiety may be a T cell receptor (TCR). TCRs are described using the International Immunogenetics (IMGT) TCR nomenclature, and links to the IMGT public database of TCR sequences. The unique sequences defined by the IMGT nomenclature are widely known and accessible to those working in the TCR field. For example, they can be found in the "T cell Receptor Factsbook", (2001) LeFranc and LeFranc, Academic Press, ISBN 0-12-441352-8; Lefranc, (2011), Cold Spring Harb Protoc 2011(6): 595-603; Lefranc, (2001), Curr Protoc Immunol Appendix 1: Appendix 10; Lefranc, (2003), Leukemia 17(1): 260-266, and on the IMGT website (www.IMGT.org)

The TCRs useful in the invention may be in any format known to those in the art. For example, the TCRs may be αβ heterodimers, or they may be in single chain format (such as those described in WO9918129). Single chain TCRs include αβ TCR polypeptides of the type: Vα-L-Vβ, Vβ-L-Vα, Vα-Cα-L-Vβ, Vα-L-Vβ-Cβ or Vα-Cα-L-Vβ-Cβ, optionally in the reverse orientation, wherein Vα and Vβ are TCR α and β variable regions respectively, Cα and Cβ are TCR α and β constant regions respectively, and L is a linker sequence. The TCR is preferably in a soluble form (i.e. having no transmembrane or cytoplasmic domains). For stability, such soluble TCRs preferably have an introduced disulfide bond between residues of the respective constant domains, as described, for example, in WO 03/020763. Preferred TCRs of this type include those which have a TRAC1 constant domain sequence and a TRBC1 or TRBC2 constant domain sequence except that Thr 48 of TRAC1 and Ser 57 of TRBC1 or TRBC2 are replaced by cysteine residues, the said cysteines forming a disulfide bond between the TRAC1 constant domain sequence and the TRBC1 or TRBC2 constant domain sequence of the TCR. It may though contain full length alpha and beta chains.

The alpha and/or beta chain constant domain may be truncated relative to the native/naturally occurring TRAC/TRBC sequences. In addition the TRAC/TRBC may contain modifications. For example, the alpha chain extracellular sequence may include a modification relative to the native/naturally occurring TRAC whereby amino acid T48 of TRAC, with reference to IMGT numbering, is replaced with C48. Likewise, the beta chain extracellular sequence may include a modification relative to the native/naturally occurring TRBC1 or TRBC2 whereby S57 of TRBC1 or TRBC2, with reference to IMGT numbering, is replaced with C57. These cysteine substitutions relative to the native alpha and beta chain extracellular sequences enable the formation of a non-native interchain disulphide bond which stabilises the refolded soluble TCR, i.e. the TCR formed by refolding extracellular alpha and beta chains (WO 03/020763). This non-native disulphide bond facilitates the display of correctly folded TCRs on phage (Li et al., Nat Biotechnol 2005 March; 23(3):349-54). In addition the use of the stable disulphide linked soluble TCR enables more convenient assessment of binding affinity and binding half-life. Alternative positions for the formation of a non-native disulphide bond are described in WO 03/020763.

TCRs useful in the invention may be engineered to include mutations. Methods for producing mutated high affinity TCR variants such as phage display and site directed mutagenesis and are known to those in the art (for example see WO 04/044004 and Li et al., Nat Biotechnol 2005 March; 23(3):349-54).

TCRs useful in the present invention may have a binding affinity for, and/or a binding half-life for, the YLEPGPVTA (SEQ ID NO:1)-HLA-A2 complex at least double that of a TCR having the extracellular alpha chain sequence SEQ ID No: 2 and the extracellular beta chain sequence SEQ ID No: 3. TCRs useful in the invention may have a $K_D$ for the complex of ≤8 μM, ≤5 μM, ≤1 μM, ≤0.1 μM, ≤0.01 μM, ≤0.001 μM, or ≤0.0001 μM and/or have a binding half-life (T½) for the complex of ≤1.5 s, ≤3 s, ≤10 s, ≤20 s, ≤40 s, ≤60 s, ≤600 s, or ≤6000 s. A preferred $K_D$ and/or binding half-life (T½) are approximately 10-100 pM and approximately 6-48 hours respectively. A particularly preferred $K_D$ and/or binding half-life (T½) are approximately 24 pM and approximately 24 hours.

Binding affinity (inversely proportional to the equilibrium constant $K_D$) and binding half-life (expressed as T½) can be determined by any appropriate method. It will be appreciated that doubling the affinity of a TCR results in halving the $K_D$. T½ is calculated as In2 divided by the off-rate ($k_{off}$). So doubling of T½ results in a halving in $k_{off}$. $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for, the YLEPGPVTA (SEQ ID NO:1)-HLA-A2 complex if a soluble form of that TCR meets that requirement. Preferably the binding affinity or binding half-life of a given TCR is measured several times, for example 3 or more times, using the same assay protocol, and an average of the results is taken. In a preferred embodiment these measurements are made using the Surface Plasmon Resonance (BIAcore) method of Example 3 of WO2011/001152. The reference gp100 TCR—having the extracellular alpha chain sequence SEQ ID No: 2 and the extracellular beta chain sequence SEQ ID No: 3—has a $K_D$ of approximately 19 μM as measured by that method, and a $k_{off}$ of approximately 1 $s^{-1}$ (i.e T½ of approximately 0.7 s).

The TCRs useful in the invention may be associated with an anti-CD3 antibody, or a functional fragment or variant of said anti-CD3 antibody, and may be as described in WO2011/001152. Antibody fragments and variants/analogues which are suitable for use in the compositions and methods described herein include but are not limited to minibodies, Fab fragments, F(ab')₂ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain).

TCR-anti CD3 fusions useful in the invention include a TCR alpha chain amino acid sequence selected from the group consisting of:

(i) the TCR alpha chain sequence of SEQ ID No: 2, wherein amino acids 1 to 109 are replaced by the sequence of SEQ ID No: 4, wherein amino acid at position 1 is S;

(ii) the TCR alpha chain sequence of SEQ ID No: 2, wherein amino acids 1 to 109 are replaced by the sequence of SEQ ID No: 4, wherein amino acid at position 1 is A;

(iii) the TCR alpha chain sequence of SEQ ID No: 2, wherein amino acids 1 to 109 are replaced by the sequence of SEQ ID No: 4, wherein amino acid at position 1 is G;

(iv) the TCR alpha chain sequence of SEQ ID No: 2, wherein amino acids 1 to 109 are replaced by the sequence of SEQ ID No: 4, wherein amino acid at position 1 is S, and the C-terminus of the alpha chain is truncated by 8 amino acids from F196 to S203 inclusive, based on the numbering of SEQ ID No: 2;

(v) the TCR alpha chain sequence of SEQ ID No: 2, wherein amino acids 1 to 109 are replaced by the sequence of SEQ ID No: 4, wherein amino acid at position 1 is A, and the C-terminus of the alpha chain is truncated by 8 amino acids from F196 to S203 inclusive, based on the numbering of SEQ ID No: 2;

(vi) the TCR alpha chain sequence of SEQ ID No: 2, wherein amino acids 1 to 109 are replaced by the sequence of SEQ ID No: 4, wherein amino acid at position 1 is G, and the C-terminus of the alpha chain is truncated by 8 amino acids from F196 to S203 inclusive, based on the numbering of SEQ ID No: 2;

and a TCR beta chain-anti-CD3 amino acid sequence selected from the group consisting of:

(vii) the TCR beta chain-anti-CD3 sequence of SEQ ID No: 5, wherein amino acids at positions 1 and 2 are D and I respectively;

(viii) the TCR beta chain-anti-CD3 sequence of SEQ ID No: 5, wherein amino acids at positions 1 and 2 are A and I respectively;

(ix) the TCR beta chain-anti-CD3 sequence of SEQ ID No: 5, wherein amino acids at positions 1 and 2 are A and Q respectively;

(x) the TCR beta chain-anti-CD3 sequence of SEQ ID No: 5, wherein amino acids at positions 1 and 2 are D and I respectively amino acids at positions 108-131 are replaced by RTSGPGDGGKGGPGKGPGGEGTKGTGPGG (SEQ ID No: 6), and amino acids at positions 254-258 are replaced by GGEGGGSEGGGS (SEQ ID No: 7);

(xi) the TCR beta chain-anti-CD3 sequence of SEQ ID No: 5, wherein amino acids at positions 1 and 2 are D and I respectively and amino acid at position 257 is a S and amino acid at position 258 is a G;

(xii) the TCR beta chain-anti-CD3 sequence of SEQ ID No: 5, wherein amino acids at positions 1 and 2 are D and I respectively and amino acid at position 256 is a S and amino acid at position 258 is a G;

(xiii) the TCR beta chain-anti-CD3 sequence of SEQ ID No: 5, wherein amino acids at positions 1 and 2 are D and I respectively and amino acid at position 255 is a S and amino acid at position 258 is a G;

(xiv) the TCR beta chain-anti-CD3 sequence of SEQ ID No: 5, wherein amino acids at positions 1 and 2 are A and Q, and wherein amino acid at position 257 is a S and amino acid at position 258 is a G;

(xv) the TCR beta chain-anti-CD3 sequence of SEQ ID No: 5, wherein amino acids at positions 1 and 2 are A and Q, and wherein amino acid at position 256 is a S and amino acid at position 258 is a G;

(xvi) the TCR beta chain-anti-CD3 sequence of SEQ ID No: 5, wherein amino acids at positions 1 and 2 are A and Q, and wherein amino acid at position 255 is a S and amino acid at position 258 is a G;

(xvii) the TCR beta chain-anti-CD3 sequence of SEQ ID No: 5, wherein amino acid at positions 1 and 2 are A and I respectively, and wherein amino acid at position 257 is a S and amino acid at position 258 is a G;

(xviii) the TCR beta chain-anti-CD3 sequence of SEQ ID No: 5, wherein amino acids at positions 1 and 2 are A and I respectively, and wherein amino acid at position 256 is a S and amino acid at position 258 is a G;

(xix) the TCR beta chain-anti-CD3 sequence of SEQ ID No: 5, wherein amino acids at positions 1 and 2 are A and I respectively, and wherein amino acid at position 255 is a S and amino acid at position 258 is a G;

Examples of such TCR-anti CD3 fusions are a TCR in which:

the alpha chain amino acid sequence is (i) and the beta chain-anti-CD3 amino acid sequence is (vii);

the alpha chain amino acid sequence is (i) and the beta chain-anti-CD3 amino acid sequence is (x);

the alpha chain amino acid sequence is (vi) and the beta chain-anti-CD3 amino acid sequence is (ix);

the alpha chain amino acid sequence is (v) and the beta chain-anti-CD3 amino acid sequence is (viii);

the alpha chain amino acid sequence is (vi) and the beta chain-anti-CD3 amino acid sequence is (vii);

the alpha chain amino acid sequence is (i) and the beta chain-anti-CD3 amino acid sequence is (xi);

the alpha chain amino acid sequence is (i) and the beta chain-anti-CD3 amino acid sequence is (xii);

the alpha chain amino acid sequence is (i) and the beta chain-anti-CD3 amino acid sequence is (xiii);

the alpha chain amino acid sequence is (vi) and the beta chain-anti-CD3 amino acid sequence is (xiv);

the alpha chain amino acid sequence is (vi) and the beta chain-anti-CD3 amino acid sequence is (xv);

the alpha chain amino acid sequence is (vi) and the beta chain-anti-CD3 amino acid sequence is (xvi);

the alpha chain amino acid sequence is (v) and the beta chain-anti-CD3 amino acid sequence is (xvii);

the alpha chain amino acid sequence is (v) and the beta chain-anti-CD3 amino acid sequence is (xviii);

the alpha chain amino acid sequence is (v) and the beta chain-anti-CD3 amino acid sequence is (xix);

the alpha chain amino acid sequence is (vi) and the beta chain-anti-CD3 amino acid sequence is (xi);

the alpha chain amino acid sequence is (vi) and the beta chain-anti-CD3 amino acid sequence is (xii); and the alpha chain amino acid sequence is (vi) and the beta chain-anti-CD3 amino acid sequence is (xiii).

A preferred TCR-anti CD3 fusion has the alpha and beta chains of SEQ ID NOs: 4 and 5 respectively. A preferred TCR-anti CD3 fusion has the alpha chain amino acid sequence of (v) and the beta chain-anti-CD3 amino acid sequence of (viii).

Alternatively, the targeting moiety may be an antibody. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term "antibody" includes antibody fragments, derivatives, functional equivalents and homologues of antibodies, humanised antibodies, including any polypeptide comprising an immunoglobulin binding domain, whether natural or wholly or partially synthetic and any polypeptide or protein having a binding domain which is, or is homologous to, an antibody binding domain. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to herein as "mAb".

It is possible to take an antibody, for example a monoclonal antibody, and use recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin (see, for instance, EP-A-184187, GB 2188638A or EP-A-239400). A hybridoma (or other cell that produces antibodies) may be subject to genetic mutation or other changes, which may or may not alter the binding specificity of antibodies produced.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature. 1989 Oct. 12; 341 (6242):544-6) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science. 1988 Oct. 21; 242(4877):423-6; Huston et al., Proc Natl Acad Sci USA. 1988 August; 85(16):5879-83); (viii) bispecific single chain Fv dimers (PCT/US92/09965) and (ix) "diabodies", multivalent or multispecific fragments constructed by gene fusion (WO94/13804; P. Hollinger et al., Proc Natl Acad Sci USA. 1993 Jul. 15; 90(14):6444-8). Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). Where bispecific antibodies are to be used, these may be conventional bispecific antibodies, which can be manufactured in a variety of ways (Hollinger & Winter, Curr Opin Biotechnol. 1993 August; 4(4):446-9), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO J. 1991 December; 10(12):3655-9). Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

The binding moiety may be an TCR-like molecule that has been designed to specifically bind a peptide—MHC complex. Of particular preference are TCR-mimic antibodies, such as, for example those described in WO2007143104 and Sergeeva et al., Blood. 2011 Apr. 21; 117(16):4262-72 and/or Dahan and Reiter. Expert Rev Mol Med. 2012 Feb. 24; 14:e6.

Also encompassed within the present invention are binding moieties based on engineered protein scaffolds. Protein scaffolds are derived from stable, soluble, natural protein structures which have been modified to provide a binding site for a target molecule of interest. Examples of engineered protein scaffolds include, but are not limited to, affibodies, which are based on the Z-domain of staphylococcal protein A that provides a binding interface on two of its a-helices (Nygren, FEBS J. 2008 June; 275(11):2668-76); anticalins, derived from lipocalins, that incorporate binding sites for small ligands at the open end of a beta-barrel fold (Skerra, FEBS J. 2008 June; 275(11):2677-83), nanobodies, and DARPins. Engineered protein scaffolds are typically targeted to bind the same antigenic proteins as antibodies, and are potential therapeutic agents. They may act as inhibitors or antagonists, or as delivery vehicles to target molecules, such as toxins, to a specific tissue in vivo (Gebauer and Skerra, Curr Opin Chem Biol. 2009 June; 13(3):245-55). Short peptides may also be used to bind a target protein. Phylomers are natural structured peptides derived from bacterial genomes. Such peptides represent a diverse array of protein structural folds and can be used to inhibit/disrupt protein-protein interactions in vivo (Watt, Nat Biotechnol. 2006 February; 24(2):177-83)].

As described above in relation to TCRs, the CD3 binding T cell redirection moiety may be an anti-CD3 antibody, or a functional fragment or variant of said anti-CD3 antibody, and may be as described in WO2011/001152.

In one embodiment of the present invention, the method comprises administering to a patient a dose of no more than 20 µg of a T cell redirecting bi-specific therapeutic in week 1, a dose of no more than 30 µg in week 2, and a dose of at least 50 µg in week 3 and subsequent weeks, wherein the TCR moiety of the bi-specific therapeutic is associated with a T cell redirecting anti-CD3 antibody or fragment thereof and has a binding affinity for, and/or a binding half-life for, the YLEPGPVTA (SEQ ID NO:1)-HLA-A2 complex at least double that of a TCR having the extracellular alpha chain sequence SEQ ID No: 2 and the extracellular beta chain sequence SEQ ID No: 3.

It is preferred if the T cell redirecting bi-specific therapeutic is administered by intravenous infusion. Alternative routes of administration include other parenteral routes, such as subcutaneous or intramuscular infusion, enteral (including oral or rectal), inhalation or intranasal routes.

The bispecific therapeutic for use in the present invention may be administered as a monotherapy. Alternatively it may be administered in combination with one or more anti-cancer therapies, preferably immuno-modulatory therapies. The potential for additional immune activation with combination therapies increases the risk of on-target off-tumour toxicities. Such therapies include:

chemotherapy agents, such as dacarbazine and temozolamide,
immunotherapeutic agents, such as interleukin-2 (IL-2) and interferon (IFN)
checkpoint inhibitors such as agents that target PD-1 or PD-L1, e.g. pembrolizumab, nivolumab, atezolizumab, avelumab and durvalumab, and agents that target CTLA-4 such as ipilimumab and tremelimumab,
BRAF inhibitors, such as vemurafenib and dabrafenib,
MEK inhibitors, such as trametinib,
TGF-β inhibitors such as galunisertib,
MET kinase inhibitors such as merestinib.

Preferred combination therapies use durvalumab, tremelimumab, galunisertib and merestinib in combination with a T cell redirecting bi-specific therapeutic as described above. Where merestinib—see WO2010011538 or similar amidophenoxyindazole as described therein—is used in combination with the bi-specific therapeutic, the dose of merestinib may be in the range of from 40 to 120 mg once daily, preferably in the range of from 80 to 120 mg once daily.

The bispecific therapeutic may be administered on its own for the first and subsequent doses, with the additional therapeutic agents being added thereafter or vice-versa. In embodiments of the present invention where a T cell redirecting bispecific therapeutic and another cancer therapy are administered in combination, the T cell redirecting bispecific therapeutic may be administered alone in weeks 1 and 2 and the other therapy added in week 3 and subsequent weeks.

Combination therapies may lead to increased immune activation including cytokine and chemokine secretion and lymphocyte trafficking, and thus increased risk of side effects such as severe hypotension. Accordingly, the dose of a T cell redirecting bispecific therapeutic may be initially given as single agent prior to combination dosing. In a preferred embodiment a dose of no more than 20 µg is administered in week 1, a dose of no more than 30 µg is administered in week 2, and a dose of at least 50 µg is administered in week 3 and subsequent weeks. Dosing of one or more additional immuno-modulatory therapies may be administered from week 3.

The present invention relates to the treatment of gp100 positive cancers. One such cancer is melanoma. Malignant melanoma continues to represent a major public health problem globally. It is estimated that almost 76,000 new diagnoses of melanoma will be made in 2016 in the United States and almost 10,000 people are expected to die of melanoma (American Cancer Society Statistics, 2016). In addition, the rate of diagnosis of melanoma continues to rise at a significant rate; according to 2015 Surveillance, Epidemiology, and End Results data, the average incidence rate rose 1.4% each year for the last decade, and melanoma is now the fifth most common cancer diagnosis in the United States. While the prognosis for patients with early stage disease is good following surgical resection, the median survival rate drops rapidly with disease progression, falling to less than one year for patients with distal metastatic disease (Garbe et al., Oncologist 2011; 16:5-24). The rising incidence of melanoma combined with poor outcomes with standard chemotherapy and early signals from immune-based therapy have led to intense investigation of novel approaches and combinations to enhance the anti-tumour immune response.

The melanoma to be treated in accordance with the present invention may be cutaneous melanoma or uveal melanoma (also known as ocular melanoma). Alternatively, it may be any one of Lentigo maligna melanoma, superficial spreading melanoma, ascral lentiginous melanoma, mucosal melanoma, nodular melanoma, polypoid melanoma, desmoplastic melanoma, amelanotic melanoma, soft-tissue melanoma, small cell melanoma with small nevus-like cells and spitzoid melanoma.

The melanoma to be treated is generally late-stage disease (advanced disease), typically characterised by metastatic lesions. For example, Stage III and/or Stage IV, (Balch et al., J Clin Oncol 2009; 27:6199-206).

Uveal melanoma (UM) is a rare type of melanoma that is biologically distinct from cutaneous melanoma. UM is an extremely malignant neoplasm that affects the vascular layers of the eye (iris, ciliary body, and choroid). Despite its rare incidence rate (representing approximately 3% of melanoma cases, approximately 4,000 cases globally per year), (Papastefanou et al., (2011) J Skin Cancer; 2011:573974). The suppressive environment and lack of activity of checkpoint inhibition in UM suggests that mobilization of activated T cells with a tumour-specific focus may have anti-tumour activity in this disease setting.

As mentioned above other non-melanoma cancers have been reported in the literature as being gp100 positive, examples being clear cell sarcoma and neurologic cancers such as some gliomas. The present invention can be used to treat such cancers.

In a further aspect, the present invention provides a method of treating gp100 positive cancer in a patient comprising administering a T cell redirecting bispecific therapeutic to said patient, wherein each dose is administered every 5-10 days, at least the first and second doses are below 40 µg and the second dose is higher than the first dose.

In a further aspect, the present invention provides a T cell redirecting bispecific therapeutic which comprises (i) a targeting moiety that binds the YLEPGPVTA (SEQ ID NO:1)-HLA-A2 complex fused to (ii) a CD3 binding T cell redirection moiety, for use in a method of treating gp100 positive cancer in a patient comprising the following sequential steps:

(a) administering to the patient a weekly dose in the range of from 10-30 μg of the bispecific therapeutic;
(b)(i) if the patient experiences grade 1 or lower treatment-related hypotension, increasing the dose administered to the patient to a weekly dose in the range of from 20-40 μg of the bispecific therapeutic, or
(b)(ii) if the patient experiences grade 2 or higher treatment-related hypotension, continuing administering to the patient a weekly dose in the range of from 10-30 μg of the bispecific therapeutic until the patient experiences grade 1 or lower treatment-related hypotension and then increasing the dose administered to the patient to a weekly dose in the range of from 20-40 μg of the bispecific therapeutic; and
(c)(i) if the patient experiences grade 1 or lower treatment-related hypotension, increasing the dose administered to the patient to a weekly dose of at least 50 μg of the bispecific therapeutic or
(c)(ii) if the patient experiences grade 2 or higher treatment-related hypotension, continuing administering to the patient a weekly dose in the range of from 20-40 μg of the bispecific therapeutic until the patient experiences grade 1 or lower treatment-related hypotension and then increasing the dose administered to the patient to a weekly dose of at least 50 μg of the bispecific therapeutic.

In this aspect, the method may further comprise, between steps (b) and (c), the step of:
(d)(i) if the patient experiences grade 1 or lower treatment-related hypotension, increasing the dose administered to the patient to a weekly dose in the range of from 30-45 μg of the bispecific therapeutic, or
(d)(ii) if the patient experiences grade 2 or higher treatment-related hypotension, continuing administering to the patient a weekly dose in the range of from 20-40 μg of the bispecific therapeutic until the patient experiences grade 1 or lower treatment-related hypotension and then increasing the dose administered to the patient to a weekly dose in the range of from 30-45 μg of the bispecific therapeutic.

The grade of hypotension may be assessed by a physician.

Preferred features of each aspect of the invention are as for each of the other aspects mutatis mutandis. It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the T cell redirecting bispecific therapeutic for use and method for treating gp100 positive cancer are specifically embraced by the present invention and are disclosed herein just as if each and every combination was individually and explicitly disclosed. The published documents mentioned herein are incorporated to the fullest extent permitted by law. Citation or identification of any document in this application is not an admission that such document is available as prior art to the present invention.

Reference is made herein to the accompanying drawings in which:

FIG. 1 shows the amino acid sequence of the alpha chain extracellular domain of the reference gp100 TCR (SEQ ID No; 2);

FIG. 2 shows the amino acid sequence of the beta chain extracellular domain of the reference gp100 TCR (SEQ ID No; 3);

FIG. 3 shows the amino acid sequence of a gp100-specific TCR α chain (SEQ ID No: 4);

FIG. 4 shows the amino acid sequence of an anti-CD3 scFv antibody fragment (bold type) fused via a linker, namely GGGGS (underlined), at the N-terminus of a gp100-specific TCR β chain (SEQ ID No 5);

FIG. 5 shows the occurrence of toxicities including severe and/or serious hypotension relative to the number of doses of IMCgp100;

FIG. 6 shows lymphocyte trafficking from the periphery following the first dose of IMCgp100;

EXAMPLES

Figure 7:
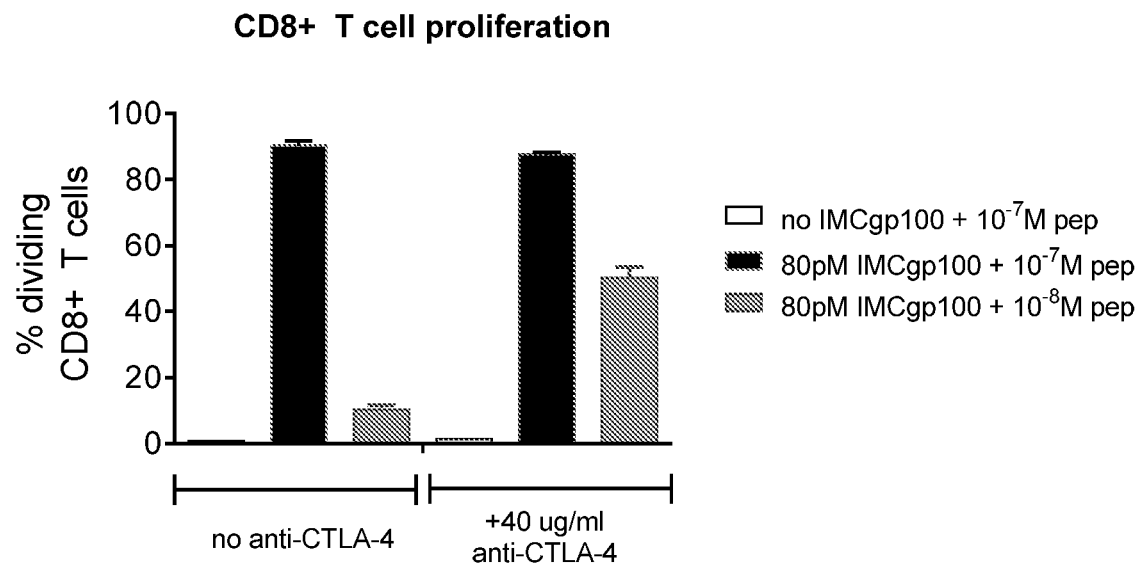
FIG. 7 shows T cell proliferation with IMCgp100 in the presence or absence anti-CTLA-4.

Example 1— Identification of a Dosage Regimen for IMCgp100 which Ameliorates Drug—Related Severe Hypotension and Allows for an Increased Upper Dose IMCgp100 is a T cell redirecting bispecific agent comprising a soluble affinity enhanced TCR that binds to the YLEPGPVTA (SEQ ID NO:1) peptide-HLA-A*02 complex, fused to an anti-CD3 scFv. [the alpha and beta chains of IMCgp100 are SEQ ID NOs 4 and 5 respectively] IMCgp100 was investigated in an first-in-human (FIH), open-label, dose finding study to assess the safety and tolerability of IMCgp100 in patients with advanced malignant melanoma (clinical trials identifier: NCT01211262). The study was designed to identify the maximum tolerated dose (MTD) or recommended Phase II dose (RP2D) of IMCgp100 in 2 repeat dosing regimens: (Arm 1) weekly dosing (the RP2D-QW) and (Arm 2) daily dosing×4 days (the RP2D-QD).

Patients with stage IV or un-resectable stage III malignant melanoma were enrolled on the study. All patients were HLA-A*02 positive, were over 18 years of age, and were classified has having measurable disease according to RECIST 1.1 criteria, with a life expectancy in excess of three months and an Eastern Cooperative Oncology Group (ECOG) performance status of 1 or below. There were no limits on the number of prior therapies. Patients were assessed for adequate haematologic, renal, hepatic, and cardiac function. Patients with symptomatic brain metastases were specifically excluded from the study. In total, 84 patients received treatment.

IMCgp100 was administered by intravenous infusion using a controlled infusion pump. Screening procedures and tests establishing eligibility were performed no more than 14 days before dosing with IMCgp100 commenced, except for HLA typing, MRI scan, ophthalmological, audiological and echocardiological assessments, which were performed within 28 days before dosing commenced. Informed consent was obtained from all patients. Blood samples for haematological, biochemical and pharmacokinetic (PK) analyses were obtained at screening, on day 1 prior to infusion, at 4, 10 and 24 hours following commencement of infusion and on days 2, 8 and 30.

Weekly Dosing: Dose Escalation Results

A standard 3+3 Phase I dose escalation protocol was followed to define the maximum tolerated dose (MTD). Briefly, the dose of IMCgp100 was escalated in cohorts of 3(+3) patients until criteria for MTD were met, or until the target limiting dose was reached. Dose escalation proceeded in three-fold increments, moving to a modified Fibonacci design according to safety and PK profile or if a dose limiting toxicity (DLT) was reported. MTD was defined as the highest dose level at which a DLT was experienced in greater than 33% of patients enrolled at that level. DLTs were observed within an 8-day window following treatment and were assessed following the NCI Common Terminology Criteria for Adverse Events (CTCAE) version 4.0. Transient Grade 3 or Grade 4 lymphopenia, and non-life threatening cutaneous skin rash were excluded as dose limiting criteria because of the anticipated pharmacological effects of the drug.

During dose escalation, 31 patients were treated across eight dose cohorts and received from 5 ng/kg to 900 ng/kg of drug. Dose limiting toxicity (DLT) of grade 3 or 4 hypotension was observed in four patients during dose escalation at 405 ng/kg (n=1 of 6), 600 ng/kg (n=1 of 6), and 900 ng/kg (n=2 of 6). In 3 of 4 DLT cases of grade 3 or 4 hypotension, the event occurred following the first dose of IMCgp100 at approximately 12-18 hours post-dose; 1 DLT hypotension event occurred with the second dose at 405 ng/kg, in a patient receiving concomitant antihypertensive therapy. Hypotension in these 4 cases was managed with IV fluids (normal saline and colloid infusions); none of the patients required pharmacologic (inotropic) support for blood pressure and all were treated with IV corticosteroid therapy. All cases of grade 3 or 4 hypotension resolved with fluid therapy and IV corticosteroid therapy within 2 days.

TABLE 1

Summary of dose limiting toxicities (DLTs) for weekly dose escalation

| Dose Level (ng/kg) | N (patients) | DLT Observed |
| --- | --- | --- |
| 5 | 3 | --- |
| 15 | 3 | --- |
| 45 | 3 | --- |
| 135 | 3 | --- |
| 270 | 3 | --- |
| 405 | 6 | One grade 3 hypotension[a] |
| 600 | 6 | One grade 4 hypotension[a] |
| 900 | 4 | Two grade 3 hypotension[a] |

DLT = dose limiting toxicity.
[a]Grade 3 and 4 hypotension was associated with a significant and rapid decrease in peripheral lymphocyte count.

Based on this data, the MTD for weekly dosing was declared at 600 ng/kg.

Weekly Dosing: RP2D-QW Cohort Results

A review of the PK and safety data from the weekly dose escalation cohorts suggested that more severe toxicities and higher drug exposures of IMCgp100 were associated with higher absolute doses administered. Based on these data and the range of absolute doses administered at MTD of 600 ng/kg (n=5 pts, range 34-66 μg QW, median dose of 54 μg), the recommended phase 2 dose of the weekly dosing regimen (designated RP2D-QW) was initially determined to be a flat dose of 50 μg administered on a weekly basis.

During this time, an additional three patients experienced adverse events involving grade 2 or greater hypotension. These events were observed to be confined to the first two doses (e.g. Cycle 1 Day 1 (C1D1) and Cycle 1 Day 8 (C1D8)) (FIG. 5). In an attempt to avoid severe hypotension events, the first dose of IMCgp100 was subsequently reduced to 40 μg; however, hypotension (at grade ¾) was observed in a further two patients following dosing at C1D1 and/or C1D8; in one patient, grade 2 hypotension was also experienced following the third dose. No cases of severe hypotension were reported following subsequent doses. It should be noted that that the inventors observed a link between the frequency and severity of hypotension and the level of gp100 expression within the patient's tumours, patients with uveal melanoma having particularly high levels of gp100 expression and therefore at higher risk of toxicity.

A further 7 patients (6 uveal and 1 cutaneous melanoma) at high risk of toxicity due to the high levels of gp100 expression within tumours were enrolled on the weekly dose expansion phase received a first dose of 20 μg (C1D1), followed by a second dose at 30 μg (C1D8), finally moving to a flat dose of 50 μg for the third dose and beyond. Surprisingly, no severe (grade ¾) hypotension was reported for these 7 patients despite their higher risk of experiencing gp100 expression mediated toxicities.

Table 2 below summarises the three dosage regimens used in the study, the number of patients treated on each regimen and the number of hypotension adverse events that were reported.

TABLE 2

Summary of weekly dosage regimens and hypotension events

| Weekly Regimen | No. patients | No. hypotension events | | |
| --- | --- | --- | --- | --- |
| | | Grade 2 | Grade 3 | Grade 4 |
| Flat dose (600/900 ng/kg/50 μg) | 35 | 4 | 4 | 1 |
| 40 μg (C1D1) - 50 μg | 3 | 2 | 2 | 0 |
| 20 μg (C1D1) - 30 μg (C1D8) -50 μg | 7 | 1 | 0 | 0 |

These data demonstrate the surprising benefit of a two-step intra-patient dose escalation regimen, in ameliorating drug-related severe hypotension when treating patients with gp100 positive cancers.

Hypotension results from lymphocyte trafficking and cytokine release

Analysis of blood from a subset of patients dosed at weekly RP2D showed marked lymphocyte trafficking after IMCgp100 had been administered. Lymphocyte levels dropped substantially at about 12-24 h post-infusion, returning to baseline levels by Day 8. This effect was more profound in cases with severe and/or serious hypotension (FIG. 6). Cytokine analyses revealed modest levels of one or more inflammatory cytokines. The greatest increases observed in the periphery were in the levels of tissue chemoattractant chemokines that parallel the transient drop in peripheral circulating lymphocytes generally resolving by 48 hours after dosing and reaching pre-dose levels by Day 8.

Further testing of intra-patient dosage regimen

A retrospective review of the tumour response data from the patients treated in the above Phase 1 study generally noted objective responses were obtained in patients who received higher absolute doses (approximately 65-85 μg). It was therefore hypothesised that using 20 μg at C1D1 and 30 μg at C1D8 may allow for higher absolute doses, i.e. above 50 μg, at Cycle 1 Day 15 (C1D15) and beyond, and potentially improve efficacy.

To test this, IMCgp100 is being further investigated in an ongoing phase I open-label, multi-centre study in patients with advanced uveal melanoma (clinical trial identifier: NCT02570308). The first part of the study follows a standard 3+3 dose escalation design. The first cohort of patients have received IMCgp100 administered by intravenous infusion at a fixed dose of 20 µg at C1D1 and 30 µg at C1D8, followed by dosing at 60 µg from C1D15. Initial data indicate no severe hypotension-related events were reported for patients in this cohort (n=3). Further cohorts of patients will receive higher doses at C1D15 (e.g. 70 µg, 80 µg or higher).

Example 2— Evidence for Increased Risk of Severe Hypotension for IMCgp100 Administered in Combination with Other Immune-Modulating Drugs IMCgp100-mediated immune activation was investigated in vitro in the presence or absence of checkpoint inhibitor antibodies against PD-L1/PD-1 and CTLA-4.

Increased potency of T cell response with IMCgp100 in combination with anti-CTLA-4 In this experiment T cell proliferation was used as read-out for potency. IMCgp100 was used at a concentration of 80 µM in the presence or absence of 40 ug/ml anti-CTLA-4 (clone L3D10; Biolegend). HLA-A*02 positive monocytes pulsed with 10 nM or 100 nM gp100 peptide were used as target antigen presenting cells and plated at 10,000 cells/well. Effector CD3$^+$ T cells were labelled with Cell Tracker Violet. T cell proliferation was measured after 5 days using the FACS based Intellicyt assay.

The results presented in FIG. 7 show that IMCgp100 in combination with anti CTLA-4 results in an improved T cell response (at lower peptide concentrations) relative to IMCgp100 alone, indicating a potential for higher levels of both efficacy and gp100 specific on-target, off-tumour toxicity in patients treated with this combination relative to IMCgp100 monotherapy.

Increased potency of T cell killing with IMCgp100 in combination with anti-PD-L1 In this experiment, T cell killing was used as read-out for potency. IMCgp100 was used at a concentration of 80 µM and 100 µM in the presence or absence of 10 ug/ml anti-PD-L1 (clone 29E.2A3; BioLegend). HLA-A*02 positive Mel624 cells were used as target antigen presenting cells. CD8+ T cells were used as effector cells at an effector target ratio of 5:1. T cell killing was measured using the Incucyte ZOOM assay over 3 days. Caspase-3/7 activation in target cells was monitored as a measure of apoptosis (imaged every 2 hours).

Figure 8:
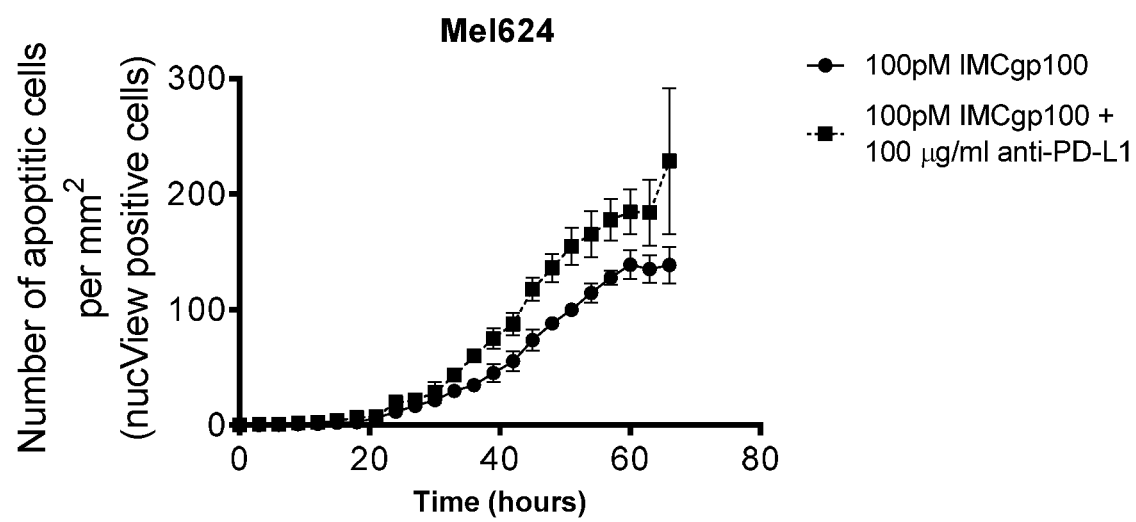
FIG. 8 shows T cell proliferation with IMCgp100 in the presence or absence of anti-PD-L1.

The results presented in FIG. 8 show that IMCgp100 in combination with anti PD-L1 results in augmented T cell killing relative to IMCgp100 alone, indicating a potential for higher levels of both efficacy and gp100 specific on-target, off-tumour toxicity in patients treated with this combination relative to IMCgp100 monotherapy.

Increased production of pro-inflammatory cytokines with IMCgp100 in combination with anti-CTLA-4 or anti-PD-L1

In this experiment, cytokine secretion was assessed using the V-PLEX human pro-inflammatory panel 1 assay kit from Meso Scale Discovery.

For IMCgp100 in combination with anti-CTLA-4 and anti-PD-L1, supernatant samples were taken at 24 h from the proliferation assay and the killing assay respectively.

Figure 9:
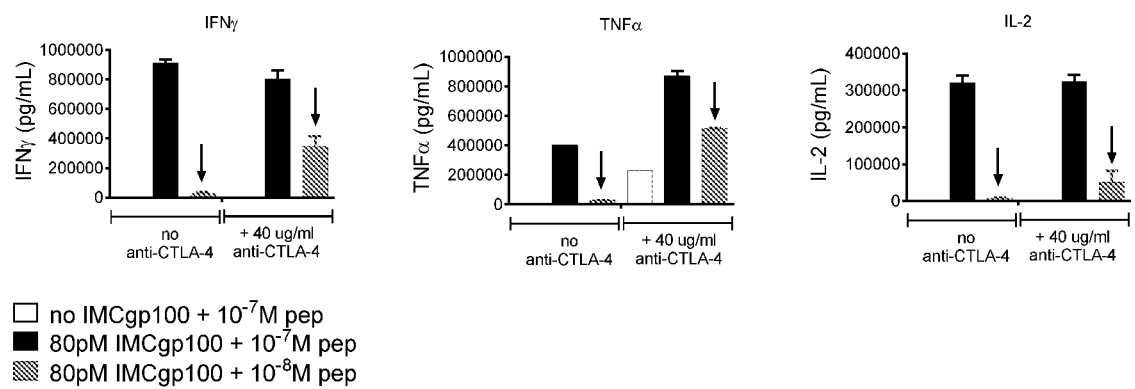
FIG. 9 shows secretion of cytokines IFNγ, TNFα and IL-2 with IMCgp100 in the presence or absence of anti-CTLA-4.

The data shown in FIG. 9 demonstrate augmented secretion of IFNγ, TNFα and IL-2 (at low peptide concentrations) in the presence of IMCgp100 and anti-CTLA-4, relative to IMCgp100 alone.

Figure 10:
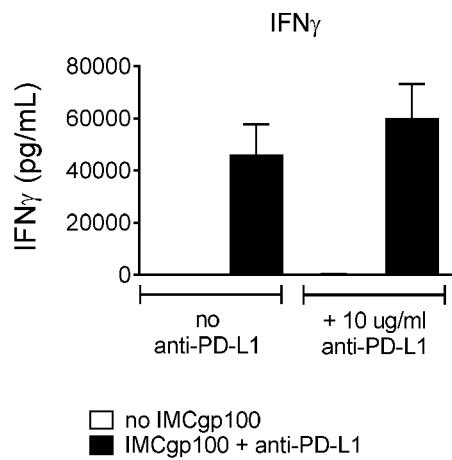
FIG. 10 shows secretion of cytokine IFNγ with IMCgp100 in the presence or absence of anti-CTLA-4.

The data shown in FIG. 10 demonstrate augmented secretion of IFNγ in the presence of IMCgp100 and anti-PD-L1, relative to IMCgp100 alone.

These data demonstrate increased immune activation with IMCgp100 combination therapy relative to IMCgp100 monotherapy, and therefore a potential increased risk of severe hypotension for patients receiving the combination therapy, due to on-target off-tumour targeting of gp100 positive melanocytes.

The invention claimed is:

1. A method of treating gp100 positive cancer in a patient, comprising:

administering to said patient a plurality of doses of a T cell redirecting bispecific therapeutic which comprises (1) a targeting moiety that binds the YLEPGPVTA (SEQ ID NO:1)-HLA-A2 complex fused to (2) a CD3 binding T cell redirection moiety, wherein the bispecific therapeutic includes (a) a TCR alpha chain amino acid sequence selected from the group consisting of:
(i) the TCR alpha chain sequence of SEQ ID No: 2, wherein amino acids 1 to 109 are replaced by the sequence of SEQ ID No: 4, wherein amino acid at position 1 is S;
(ii) the TCR alpha chain sequence of SEQ ID No: 2, wherein amino acids 1 to 109 are replaced by the sequence of SEQ ID No: 4, wherein amino acid at position 1 is A;
(iii) the TCR alpha chain sequence of SEQ ID No: 2, wherein amino acids 1 to 109 are replaced by the sequence of SEQ ID No: 4, wherein amino acid at position 1 is G;
(iv) the TCR alpha chain sequence of SEQ ID No: 2, wherein amino acids 1 to 109 are replaced by the sequence of SEQ ID No: 4, wherein amino acid at position 1 is S, and the C-terminus of the alpha chain is truncated by 8 amino acids from F196 to S203 inclusive, based on the numbering of SEQ ID No: 2;
(v) the TCR alpha chain sequence of SEQ ID No: 2, wherein amino acids 1 to 109 are replaced by the sequence of SEQ ID No: 4, wherein amino acid at position 1 is A, and the C-terminus of the alpha chain is truncated by 8 amino acids from F196 to S203 inclusive, based on the numbering of SEQ ID No: 2; and
(vi) the TCR alpha chain sequence of SEQ ID No: 2, wherein amino acids 1 to 109 are replaced by the sequence of SEQ ID No: 4, wherein amino acid at position 1 is G, and the C-terminus of the alpha chain is truncated by 8 amino acids from F196 to S203 inclusive, based on the numbering of SEQ ID No: 2; and (b) a TCR beta chain-anti-CD3 amino acid sequence selected from the group consisting of:
(vii) the TCR beta chain-anti-CD3 sequence of SEQ ID No: 5, wherein amino acids at positions 1 and 2 are D and I respectively;
(viii) the TCR beta chain-anti-CD3 sequence of SEQ ID No: 5, wherein amino acids at positions 1 and 2 are A and I respectively;
(ix) the TCR beta chain-anti-CD3 sequence of SEQ ID No: 5, wherein amino acids at positions 1 and 2 are A and Q respectively;

27

(x) the TCR beta chain-anti-CD3 sequence of SEQ ID No: 5, wherein amino acids at positions 1 and 2 are D and I respectively amino acids at positions 108-131 are replaced by RTSGPGDGGKGGPGKGPGGEGTKGTGPGG (SEQ ID No: 6), and amino acids at positions 254-258 are replaced by GGEGGGSEGGGS (SEQ ID No: 7);

(xi) the TCR beta chain-anti-CD3 sequence of SEQ ID No: 5, wherein amino acids at positions 1 and 2 are D and I respectively and amino acid at position 257 is a S and amino acid at position 258 is a G;

(xii) the TCR beta chain-anti-CD3 sequence of SEQ ID No: 5, wherein amino acids at positions 1 and 2 are D and I respectively and amino acid at position 256 is a S and amino acid at position 258 is a G;

(xiii) the TCR beta chain-anti-CD3 sequence of SEQ ID No: 5, wherein amino acids at positions 1 and 2 are D and I respectively and amino acid at position 255 is a S and amino acid at position 258 is a G;

(xiv) the TCR beta chain-anti-CD3 sequence of SEQ ID No: 5, wherein amino acids at positions 1 and 2 are A and Q, and wherein amino acid at position 257 is a S and amino acid at position 258 is a G;

(xv) the TCR beta chain-anti-CD3 sequence of SEQ ID No: 5, wherein amino acids at positions 1 and 2 are A and Q, and wherein amino acid at position 256 is a S and amino acid at position 258 is a G;

(xvi) the TCR beta chain-anti-CD3 sequence of SEQ ID No: 5, wherein amino acids at positions 1 and 2 are A and Q, and wherein amino acid at position 255 is a S and amino acid at position 258 is a G;

(xvii) the TCR beta chain-anti-CD3 sequence of SEQ ID No: 5, wherein amino acid at positions 1 and 2 are A and I respectively, and wherein amino acid at position 257 is a S and amino acid at position 258 is a G;

(xviii) the TCR beta chain-anti-CD3 sequence of SEQ ID No: 5, wherein amino acid at positions 1 and 2 are A and I respectively, and wherein amino acid at position 256 is a S and amino acid at position 258 is a G; and (xix) the TCR beta chain-anti-CD3 sequence of SEQ ID No: 5, wherein amino acid at positions 1 and 2 are A and I respectively, and wherein amino acid at position 255 is a S and amino acid at position 258 is a G; and wherein the method comprises administration of:
(a) at least one first dose in the range of from 10-30 fig;
(b) at least one second dose in the range of from 20-40 μg, wherein the second dose is higher than the first dose; and then
(c) at least one dose of at least 50 μg.

2. The method of claim 1, wherein the plurality of doses of the T cell redirecting bispecific therapeutic are administered at a dosing interval of 7 days.

3. The method of claim 1, wherein the first dose is 20 μg, the second dose is 30 μg and the dose after the second dose is at least 50 μg.

4. The method of claim 1, wherein two second doses are administered.

5. The method of claim 1, wherein the TCR has a binding affinity for, and/or a binding half-life for, the YLEPGPVTA (SEQ ID NO:1)-HLA-A2 complex at least double that of a TCR having an extracellular alpha chain sequence SEQ ID No: 2 and an extracellular beta chain sequence SEQ ID No: 3.

6. The method of claim 1, wherein:
the alpha chain amino acid sequence is (i) and the beta chain-anti-CD3 amino acid sequence is (vii);

28 the alpha chain amino acid sequence is (i) and the beta chain-anti-CD3 amino acid sequence is (x);
the alpha chain amino acid sequence is (vi) and the beta chain-anti-CD3 amino acid sequence is (ix);
the alpha chain amino acid sequence is (v) and the beta chain-anti-CD3 amino acid sequence is (viii);
the alpha chain amino acid sequence is (vi) and the beta chain-anti-CD3 amino acid sequence is (vii);
the alpha chain amino acid sequence is (i) and the beta chain-anti-CD3 amino acid sequence is (xi);
the alpha chain amino acid sequence is (i) and the beta chain-anti-CD3 amino acid sequence is (xii);
the alpha chain amino acid sequence is (i) and the beta chain-anti-CD3 amino acid sequence is (xiii);
the alpha chain amino acid sequence is (vi) and the beta chain-anti-CD3 amino acid sequence is (xiv);
the alpha chain amino acid sequence is (vi) and the beta chain-anti-CD3 amino acid sequence is (xv);
the alpha chain amino acid sequence is (vi) and the beta chain-anti-CD3 amino acid sequence is (xvi);
the alpha chain amino acid sequence is (v) and the beta chain-anti-CD3 amino acid sequence is (xvii);
the alpha chain amino acid sequence is (v) and the beta chain-anti-CD3 amino acid sequence is (xviii);
the alpha chain amino acid sequence is (v) and the beta chain-anti-CD3 amino acid sequence is (xix);
the alpha chain amino acid sequence is (vi) and the beta chain-anti-CD3 amino acid sequence is (xi);
the alpha chain amino acid sequence is (vi) and the beta chain-anti-CD3 amino acid sequence is (xii); or
the alpha chain amino acid sequence is (vi) and the beta chain-anti-CD3 amino acid sequence is (xiii).

7. The method of claim 6, wherein the alpha chain amino acid sequence is (v) and the beta chain-anti-CD3 amino acid sequence is (viii).

8. The method of claim 1, wherein the bispecific therapeutic is administered in combination with one or more anti-cancer therapies.

9. The method of claim 8, wherein the anti-cancer therapy is durvalumab, tremelimumab, galunisertib and merestinib.

10. The method of claim 9, wherein the anti-cancer therapy is merestinib and wherein the dose of merestinib is in the range of 40 to 120 mg once daily.

11. The method of claim 1, wherein the gp100 positive cancer is melanoma.

12. The method of claim 9, wherein the anti-cancer therapy is merestinib and the dose of merestinib is in the range of 80 to 120 mg once daily.

13. A method of treating gp100 positive cancer in a patient, comprising:
administering to said patient a plurality of doses of a T cell redirecting bispecific therapeutic at a dosing interval of 7 days, wherein the T cell redirecting bispecific therapeutic comprises (1) a TCR that binds to the YLEPGPVTA (SEQ ID NO:1)-HLA-A2 complex, fused to (2) an anti-CD3 antibody, wherein the bispecific therapeutic includes
(a) a TCR alpha chain amino acid sequence as provided in SEQ ID No: 4; and
(b) a TCR beta chain-anti-CD3 sequence as provided in SEQ ID No: 5, and wherein
the method comprises administration of:
(a) at least one first dose of 20 μg;
(b) at least one second dose of 30 μg; and then
(c) at least one dose of at least 50 μg.

14. The method of claim 13, wherein the gp100 positive cancer is uveal melanoma.

* * * * *

UNITED STATES PATENT AND TRADEMARK OFFICE
CERTIFICATE OF CORRECTION

PATENT NO. : 11,827,688 B2  Page 1 of 2
APPLICATION NO. : 16/305838
DATED : November 28, 2023
INVENTOR(S) : Christina Coughlin It is certified that error appears in the above-identified patent and that said Letters Patent is hereby corrected as shown below:

In the Drawings

Sheet 1 of 5, FIG. 1, Line 2, delete "(SEQ ID No; 2);" and insert -- (SEQ ID No: 2); --, therefor.

Sheet 1 of 5, FIG. 2, Line 2, delete "(SEQ ID No; 3);" and insert -- (SEQ ID No: 3); --, therefor.

Sheet 2 of 5, FIG. 3, Line 2, delete "(SEQ ID No: 4):" and insert -- (SEQ ID No: 4); --, therefor.

Sheet 2 of 5, FIG. 4, Lines 2-3, delete "(SEQ ID No 5):" and insert -- (SEQ ID No: 5); --, therefor.

Sheet 4 of 5, FIG. 8, delete "apoptitic cells" and insert -- apoptotic cells --, therefor.

In the Specification

In Column 1, Line 57, delete "315-323.))." and insert -- 315-323)). --, therefor.

In Column 2, Line 11, delete "gp100+/HLA-A*02+" and insert -- gp100*/HLA-A*02$^+$ --, therefor.

In Column 6, Lines 34-35, delete "$\leq$1.5 s, $\leq$3 s, $\leq$10 s, $\leq$20 s, $\leq$40 s, $\leq$60 s, $\leq$600 s, or $\leq$6000 s." and insert -- $\geq$1.5 s, $\geq$3 s, $\geq$10 s, $\geq$20 s, $\geq$40 s, $\geq$60 s, $\geq$600 s, or $\geq$6000 s. --, therefor.

In Column 6, Line 45, delete "T %" and insert -- T½ --, therefor.

In Column 11, Line 2, delete "177-83)]." and insert -- 177-83). --, therefor.

In Column 11, Lines 31-32, delete "temozolamide," and insert -- temozolomide, --, therefor.

In Column 11, Line 34, delete "IFN)" and insert -- IFN), --, therefor.

In Column 12, Line 29, delete "maligna melanoma," and insert -- malignant melanoma, --, therefor.

Signed and Sealed this
Eighteenth Day of March, 2025

Coke Morgan Stewart
*Acting Director of the United States Patent and Trademark Office*

CERTIFICATE OF CORRECTION (continued)
U.S. Pat. No. 11,827,688 B2

In Column 12, Line 30, delete "ascral" and insert -- acral --, therefor.

In Column 13, Line 64, delete "No; 2);" and insert -- No: 2); --, therefor.

In Column 13, Line 67, delete "No; 3);" and insert -- No: 3); --, therefor.

In Column 14, Line 16, delete "anti-PD-L1," and insert -- anti-PD-L1; --, therefor.

In Column 16, Line 7, delete "that that" and insert -- that --, therefor.

In Column 27, Line 46, delete "10-30 fig;" and insert -- 10-30 μg; --, therefor.

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Amino acid residues 280-288 of gp100

<400> SEQUENCE: 1

Tyr Leu Glu Pro Gly Pro Val Thr Ala
1               5

<210> SEQ ID NO 2
<211> LENGTH: 203
<212> TYPE: PRT
<213> ORGANISM: Artificial Sequence
<220> FEATURE:
<223> OTHER INFORMATION: Amino acid sequence of the alpha chain
      extracellular domain of the reference gp100 TCR

<400> SEQUENCE: 2

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
```

```
                    20                  25                  30
Gln Trp Tyr Arg Gln Asn Ser Gly Arg Gly Leu Val His Leu Ile Leu
                35                  40                  45
Ile Arg Ser Asn Glu Arg Glu Lys His Ser Gly Arg Leu Arg Val Thr
 50                  55                  60
Leu Asp Thr Ser Lys Lys Ser Ser Ser Leu Leu Ile Thr Ala Ser Arg
 65                  70                  75                  80
Ala Ala Asp Thr Ala Ser Tyr Phe Cys Ala Thr Asp Gly Asp Thr Pro
                85                  90                  95
Leu Val Phe Gly Lys Gly Thr Arg Leu Ser Val Ile Ala Asn Ile Gln
                100                 105                 110
Lys Pro Asp Pro Ala Val Tyr Gln Leu Arg Asp Ser Lys Ser Ser Asp
                115                 120                 125
Lys Ser Val Cys Leu Phe Thr Asp Phe Asp Ser Gln Thr Asn Val Ser
                130                 135                 140
Gln Ser Lys Asp Ser Asp Val Tyr Ile Thr Asp Lys Cys Val Leu Asp
145                 150                 155                 160
Met Arg Ser Met Asp Phe Lys Ser Asn Ser Ala Val Ala Trp Ser Asn
                165                 170                 175
Lys Ser Asp Phe Ala Cys Ala Asn Ala Phe Asn Asn Ser Ile Ile Pro
                180                 185                 190
Glu Asp Thr Phe Phe Pro Ser Pro Glu Ser Ser
                195                 200

<210> SEQ ID NO 3
<211> LENGTH: 242
<212> TYPE: PRT
<213> ORGANISM: Artificial Sequence
<220> FEATURE:
<223> OTHER INFORMATION: Amino acid sequence of the beta chain
      extracellular domain of the reference gp100 TCR

<400> SEQUENCE: 3

Asp Gly Gly Ile Thr Gln Ser Pro Lys Tyr Leu Phe Arg Lys Glu Gly
 1               5                  10                  15
Gln Asn Val Thr Leu Ser Cys Glu Gln Asn Leu Asn His Asp Ala Met
                20                  25                  30
Tyr Trp Tyr Arg Gln Asp Pro Gly Gln Gly Leu Arg Leu Ile Tyr Tyr
                35                  40                  45
Ser Gln Ile Val Asn Asp Phe Gln Lys Gly Asp Ile Ala Glu Gly Tyr
 50                  55                  60
Ser Val Ser Arg Glu Lys Lys Glu Ser Phe Pro Leu Thr Val Thr Ser
 65                  70                  75                  80
Ala Gln Lys Asn Pro Thr Ala Phe Tyr Leu Cys Ala Ser Ser Ile Gly
                85                  90                  95
Gly Pro Tyr Glu Gln Tyr Phe Gly Pro Gly Thr Arg Leu Thr Val Thr
                100                 105                 110
Glu Asp Leu Lys Asn Val Phe Pro Pro Glu Val Ala Val Phe Glu Pro
                115                 120                 125
Ser Glu Ala Glu Ile Ser His Thr Gln Lys Ala Thr Leu Val Cys Leu
130                 135                 140
Ala Thr Gly Phe Tyr Pro Asp His Val Glu Leu Ser Trp Trp Val Asn
145                 150                 155                 160
Gly Lys Glu Val His Ser Gly Val Cys Thr Asp Pro Gln Pro Leu Lys
                165                 170                 175
```

Glu Gln Pro Ala Leu Asn Asp Ser Arg Tyr Ala Leu Ser Ser Arg Leu
                180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
        210                 215                 220

Arg Ala Lys Pro Val Thr Gln Ile Val Ser Ala Glu Ala Trp Gly Arg
225                 230                 235                 240

Ala Asp

<210> SEQ ID NO 4
<211> LENGTH: 195
<212> TYPE: PRT
<213> ORGANISM: Artificial Sequence
<220> FEATURE:
<223> OTHER INFORMATION: Amino acid sequence of a gp100-specific TCR
      alpha chain

<400> SEQUENCE: 4

Ala Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
        50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Gly Ser Thr Pro
                85                  90                  95

Met Gln Phe Gly Lys Gly Thr Arg Leu Ser Val Ile Ala Asn Ile Gln
            100                 105                 110

Lys Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
130                 135                 140

Gln Ser Lys Asp Ser Asp Val Tyr Ile Thr Asp Lys Cys Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr
        195

<210> SEQ ID NO 5
<211> LENGTH: 500
<212> TYPE: PRT
<213> ORGANISM: Artificial Sequence
<220> FEATURE:
<223> OTHER INFORMATION: Amino acid sequence of an anti-CD3 scFv
      antibody fragment fused via a linker namely GGGGS at the
      N-terminus of a gp100-specific TCR beta chain

<400> SEQUENCE: 5

Ala Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Arg Asn Tyr
            20                  25                  30
Leu Asn Trp Tyr Gln Gln Lys Pro Gly Lys Ala Pro Lys Leu Leu Ile
            35                  40                  45
Tyr Tyr Thr Ser Arg Leu Glu Ser Gly Val Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Tyr Cys Gln Gln Gly Asn Thr Leu Pro Trp
                85                  90                  95
Thr Phe Gly Gln Gly Thr Lys Val Glu Ile Lys Gly Gly Gly Gly Ser
                100                 105                 110
Gly Gly Gly Gly Ser Gly Gly Gly Ser Gly Gly Gly Gly Ser Gly
            115                 120                 125
Gly Gly Ser Glu Val Gln Leu Val Glu Ser Gly Gly Gly Leu Val Gln
            130                 135                 140
Pro Gly Gly Ser Leu Arg Leu Ser Cys Ala Ala Ser Gly Tyr Ser Phe
145                 150                 155                 160
Thr Gly Tyr Thr Met Asn Trp Val Arg Gln Ala Pro Gly Lys Gly Leu
                165                 170                 175
Glu Trp Val Ala Leu Ile Asn Pro Tyr Lys Gly Val Ser Thr Tyr Asn
                180                 185                 190
Gln Lys Phe Lys Asp Arg Phe Thr Ile Ser Val Asp Lys Ser Lys Asn
                195                 200                 205
Thr Ala Tyr Leu Gln Met Asn Ser Leu Arg Ala Glu Asp Thr Ala Val
            210                 215                 220
Tyr Tyr Cys Ala Arg Ser Gly Tyr Tyr Gly Asp Ser Asp Trp Tyr Phe
225                 230                 235                 240
Asp Val Trp Gly Gln Gly Thr Leu Val Thr Val Ser Ser Gly Gly Gly
                245                 250                 255
Gly Ser Asp Gly Gly Ile Thr Gln Ser Pro Lys Tyr Leu Phe Arg Lys
            260                 265                 270
Glu Gly Gln Asn Val Thr Leu Ser Cys Glu Gln Asn Leu Asn His Asp
            275                 280                 285
Ala Met Tyr Trp Tyr Arg Gln Asp Pro Gly Gln Gly Leu Arg Leu Ile
            290                 295                 300
Tyr Tyr Ser Trp Ala Gln Gly Asp Phe Gln Lys Gly Asp Ile Ala Glu
305                 310                 315                 320
Gly Tyr Ser Val Ser Arg Glu Lys Lys Glu Ser Phe Pro Leu Thr Val
                325                 330                 335
Thr Ser Ala Gln Lys Asn Pro Thr Ala Phe Tyr Leu Cys Ala Ser Ser
            340                 345                 350
Trp Gly Ala Pro Tyr Glu Gln Tyr Phe Gly Pro Gly Thr Arg Leu Thr
            355                 360                 365
Val Thr Glu Asp Leu Lys Asn Val Phe Pro Pro Glu Val Ala Val Phe
            370                 375                 380
Glu Pro Ser Glu Ala Glu Ile Ser His Thr Gln Lys Ala Thr Leu Val
385                 390                 395                 400
Cys Leu Ala Thr Gly Phe Tyr Pro Asp His Val Glu Leu Ser Trp Trp
                405                 410                 415
Val Asn Gly Lys Glu Val His Ser Gly Val Cys Thr Asp Pro Gln Pro
            420                 425                 430
Leu Lys Glu Gln Pro Ala Leu Asn Asp Ser Arg Tyr Ala Leu Ser Ser
```

```
                     435                 440                 445
Arg Leu Arg Val Ser Ala Thr Phe Trp Gln Asp Pro Arg Asn His Phe
    450                 455                 460

Arg Cys Gln Val Gln Phe Tyr Gly Leu Ser Glu Asn Asp Glu Trp Thr
465                 470                 475                 480

Gln Asp Arg Ala Lys Pro Val Thr Gln Ile Val Ser Ala Glu Ala Trp
                485                 490                 495

Gly Arg Ala Asp
            500

<210> SEQ ID NO 6
<211> LENGTH: 29
<212> TYPE: PRT
<213> ORGANISM: Artificial Sequence
<220> FEATURE:
<223> OTHER INFORMATION: Amino acid sequence to replace amino acids at
      positions 108-131 of SEQ ID NO: 5

<400> SEQUENCE: 6

Arg Thr Ser Gly Pro Gly Asp Gly Gly Lys Gly Gly Pro Gly Lys Gly
1               5                   10                  15

Pro Gly Gly Glu Gly Thr Lys Gly Thr Gly Pro Gly Gly
            20                  25

<210> SEQ ID NO 7
<211> LENGTH: 12
<212> TYPE: PRT
<213> ORGANISM: Artificial Sequence
<220> FEATURE:
<223> OTHER INFORMATION: Amino acid sequence to replace amino acids at
      positions 254-258 of SEQ ID No: 5

<400> SEQUENCE: 7

Gly Gly Glu Gly Gly Gly Ser Glu Gly Gly Gly Ser
1               5                   10
```